US011767362B1

(12) United States Patent
Endo et al.

(10) Patent No.: US 11,767,362 B1
(45) Date of Patent: Sep. 26, 2023

(54) METHODS OF TREATING CANCERS USING PD-1 AXIS BINDING ANTAGONISTS AND ANTI-GPC3 ANTIBODIES

(71) Applicants: Chugai Seiyaku Kabushiki Kaisha, Tokyo (JP); Genentech, Inc., South San Francisco, CA (US)

(72) Inventors: Mika Endo, Kanagawa (JP); Atsuhiko Kato, Shizuoka (JP); Toshihiko Ohtomo, Tokyo (JP); Kenji Adachi, Shizuoka (JP); Yasuko Kinoshita, Kanagawa (JP); Yoshinori Narita, Kanagawa (JP)

(73) Assignees: Chugai Seiyaku Kabushiki Kaisha, Tokyo (JP); Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/084,346

(22) PCT Filed: Mar. 14, 2017

(86) PCT No.: PCT/JP2017/010267
§ 371 (c)(1),
(2) Date: Sep. 12, 2018

(87) PCT Pub. No.: WO2017/159699
PCT Pub. Date: Sep. 21, 2017

(30) Foreign Application Priority Data

Mar. 15, 2016 (JP) .................. 2016-051424

(51) Int. Cl.
C07K 16/28 (2006.01)
C07K 16/30 (2006.01)
A61P 35/00 (2006.01)

(52) U.S. Cl.
CPC .......... *C07K 16/2827* (2013.01); *A61P 35/00* (2018.01); *C07K 16/303* (2013.01); *C07K 2317/24* (2013.01); *C07K 2317/54* (2013.01); *C07K 2317/55* (2013.01); *C07K 2317/56* (2013.01); *C07K 2317/622* (2013.01); *C07K 2317/76* (2013.01)

(58) Field of Classification Search
CPC ............. C07K 16/2827; C07K 16/303; C07K 2317/24; C07K 2317/54; C07K 2317/55; C07K 2317/56; C07K 2317/622; C07K 2317/76; A61P 35/00
See application file for complete search history.

(56) References Cited

U.S. PATENT DOCUMENTS

| 7,919,086 B2 | 4/2011 | Nakano et al. |
| 2004/0236080 A1 | 11/2004 | Aburatani et al. |
| 2007/0087005 A1 | 4/2007 | Lazar et al. |
| 2007/0190599 A1* | 8/2007 | Nakano ............. A61P 1/16 435/69.1 |
| 2008/0124330 A1 | 5/2008 | Nakano et al. |
| 2010/0203056 A1 | 8/2010 | Irving et al. |
| 2010/0239577 A1 | 9/2010 | Igawa et al. |
| 2011/0104157 A1 | 5/2011 | Kinoshita et al. |
| 2014/0341902 A1* | 11/2014 | Maecker ........... A61K 31/4184 424/135.1 |
| 2015/0203580 A1 | 7/2015 | Papadopoulos et al. |
| 2015/0216970 A1 | 8/2015 | Grogan et al. |
| 2015/0285806 A1 | 10/2015 | Toshihiko et al. |
| 2016/0009805 A1* | 1/2016 | Kowanetz ............ A61K 45/06 530/391.1 |
| 2016/0319022 A1 | 11/2016 | Yang et al. |
| 2019/0309071 A1 | 10/2019 | Mariathasan et al. |

FOREIGN PATENT DOCUMENTS

| CA | 2994751 A1 | 2/2017 |
| CN | 102180969 A | 9/2011 |
| CN | 102702353 A | 10/2012 |
| CN | 102850455 A | 1/2013 |
| EP | 2275135 A1 | 1/2011 |
| JP | 2012511329 A | 5/2012 |
| JP | 2016533335 A | 10/2016 |
| JP | 2017507650 A | 3/2017 |
| JP | 6430025 B2 | 11/2018 |
| WO | WO-2003000883 A1 | 1/2003 |
| WO | WO-2006006693 A1 | 1/2006 |
| WO | WO-2006046751 A1 | 5/2006 |
| WO | WO-2007047291 A2 | 4/2007 |
| WO | WO-2009041062 A1 | 4/2009 |

(Continued)

OTHER PUBLICATIONS

Klein et al. (mAbs, 5(1): 22-33, 2013).*
Chodorge et al. (Cell Death and Differentiation, 19: 1187-1195, 2012).*
Llovet, J. M., et al., "Hepatocellular carcinoma," The Lancet 362:1907-1917 (2003).
Bosch, F. X., et al., "Primary Liver Cancer: Worldwide Incidence and Trends," Gastroenterology 127:S5-S16 (2004).
Takenaka, K., et al., "Results of 280 Liver Resections for Hepatocellular Carcinoma," Arch Surg 131:71-76 (1996).

(Continued)

*Primary Examiner* — Nelson B Moseley, II
(74) *Attorney, Agent, or Firm* — Nixon & Vanderhye P.C.

(57) ABSTRACT

The invention provides compositions and methods for treating cancers. The methods comprising administering a PD-1 axis binding antagonist and an anti-GPC3 antibody. The compositions comprising a pharmaceutical composition for treating cancer which comprises a PD-1 axis binding antagonist and an anti-GPC3 antibody. Also disclosed are a pharmaceutical composition to be used in combination with a PD-1 axis binding antagonist for treating cancer which comprises an anti-GPC3 antibody as the active ingredient; and a pharmaceutical composition to be used in combination with an anti-GPC3 antibody for treating cancer which comprises as the active ingredient a PD-1 axis binding antagonist.

8 Claims, 17 Drawing Sheets
Specification includes a Sequence Listing.

(56) References Cited

FOREIGN PATENT DOCUMENTS

| WO | WO-2009122667 A1 | 10/2009 | |
|---|---|---|---|
| WO | WO-2015048520 A1 | 4/2015 | |
| WO | WO-2015051199 A2 | 4/2015 | |
| WO | WO2015095418 A1 | 6/2015 | |
| WO | WO 2015/112805 * | 7/2015 | ............. C07K 16/28 |
| WO | WO-2015112805 A1 | 7/2015 | |
| WO | WO-2015142675 A2 | 9/2015 | |
| WO | WO-2016007235 A1 | 1/2016 | |
| WO | WO-2017005771 A1 | 1/2017 | |
| WO | WO-2017020812 A1 | 2/2017 | |
| WO | WO-2017159699 A1 | 9/2017 | |

OTHER PUBLICATIONS

Yeo, W., et al., "Randomized Phase III Study of Doxorubicin Versus Cisplatin/Interferon α- 2b/Doxorubicin/Fluorouracil (PIAF) Combination Chemotherapy for Unresectable Hepatocellular Carcinoma," J Natl Cancer Inst 97:1532-1538 (2005).

Llovet, J. M., et al., "Sorafenib in Advanced Hepatocelluar Carcinoma," N Engl J Med 359:378-390 (2008).

Cheng, A.-L., et al., "Efficacy and safety of sorafenib in patients in the Asia-Pacific region with advanced hepatocellular carcinoma: a phase III randomized, double-blind, placebo-controlled trial," Lancet Oncol 10:25-34 (2009).

Lafferty, K. J. and Cunningham, A. J., "A New Analysis of Allogeneic Interactions," The Australian Journal of Experimental Biology and Medical Science 53(1):27-42 (1975).

Bretscher, P. and Cohn, M., "A Theory of Self-Nonself Discrimination," Science 169(3950):1042-1049 (1970).

Bretscher, P., "A two-step, two-signal model for the primary activation of precursor helper T cells," Proc Natl Acad Sci 96:185-190 (1999).

Jenkins, M. K. and Schwartz, R. H., "Antigen Presentation by Chemically Modified Splenocytes Induces Antigen-Specific T Cell Unresponsiveness In Vitro and In Vivo," J Exp Med 165:302-319 (1987).

Lenschow, D. J., et al., "CD28/B7 System of T Cell Costimulation," Annu Rev Immunol 14:233-258 (1996).

Okazaki, T. and Honjo, T., "PD-1 and PD-1 ligands: from discovery to clinical application," Intl Immunol 19(7):813-824 (2007).

Thompson, R. H., et al., "Tumor B7-H1 Is Associated with Poor Prognosis in Renal Cell Carcinoma Patients with Long-term Follow-up," Cancer Res 66(7):3381-3385 (2006).

Ahmadzadeh, M., et al., "Tumor antigen-specific CD8 T cells infiltrating the tumor express high levels of PD-1 and are functionally impaired," Blood 114:1537-1544 (2009).

Sharpe, A. H. and Freeman, G. J., "The B7-CD28 Superfamily," Nat Rev Immunol 2:116-126 (2002).

Keir, M. E., et al., "PD-1 and Its Ligands in Tolerance and Immunity," Annu Rev Immunol 26:677-704 (2008).

Abou-Alfa, G. K., et al., "Phase b study of RO5137382/GC33 in combination with sorafenib in patients with advanced hepatocellular carcinoma (HCC)(NCT00976170)," 2014 ASCO Annual Meeting, J Clin Oncol 32:5s (suppl; abstr 4100)(2014).

Sawada, Y., et al., "Programmed death-1 blockade enhances the antitumor effects of peptide vaccine-induced peptide-specific cytotoxic T lymphocytes," Intl J Oncol 46:28-36 (2015).

Chugai Pharmaceutical Co., Ltd., NIPH Clinical Trials Search, "A Phase I Study of Codrituzumab, in Combination With a Tezolizumab in Patients With Hepatocellular Carcinoma," Japic ID: JapicCTI-163325 (2016).

Zhu, A. X., et al., "First-in-Man Phase I Study of GC33, a Novel Recombinant Humanized Antibody Against Glypican-3, in Patients with Advanced Hepatocellular Carcinoma," Clin Cancer Res 19(4):920-928 (2012).

Chugai Pharmaceutical Co., Ltd., Japic Clinical Trials Information, "Multicenter open-label dose-escalation Phase I study of Codrituzumab (anti-Glypican-3 monoclonal antibody) with Atezolizumab in patients with locally advanced/metastatic hepatocellular carcinoma," JapicCTI-No. JapicCTI-163325 (2016).

International Search Report in International Application No. PCT/JP2017/010267, dated May 31, 2017.

Abou-Alfa, G. K., et al., "Phase Ib study of codrituzumab in combination with sorafenib in patients with non-curable advanced hepatocellular carcinoma (HCC)," Cancer Chemother Pharmacol., 79:421-429 (2017).

International Search Report dated Feb. 15, 2019 in International Application No. PCT/JP2018/036161.

GenBank, Assession Number/NCBI Reference Sequence: NP_054862. 1, "Programmed death-ligand 1 expression and its associations with clinicopathological features, prognosis, and driver oncogene alterations in surgically resected lung adenocarcinoma," published Oct. 31, 2021.

Green, M. A., et al., "Drug Monographs: Atezolizumab and Everolimus," Hosp Pharm., 51(10):810-814 (2016).

Kudo, M., "Immune Checkpoint Blockade in Hepatocellular Carcinoma," Liver Cancer, 4:201-207 (2015).

Nishida, T. and Kataoka, H., "Glypican 3-Targeted Therapy in Hepatocellular Carcinoma," Cancers, 11:1339 (2019).

Okudaira, K., et al., "Blockade of B7-H1 or B7-DC induces an anti-tumor effect in a mouse pancreatic cancer model," International Journal of Oncology, 35:741-749 (2009).

Sun, L., et al., "Clinical efficacy and safety of anti-PD-1/PD-L1 inhibitors for the treatment of advanced or metastatic cancer: a systematic review and meta-analysis," Sci Rep., 10:2083 (2020).

Iyakusearch, Japic Clinical Trials Information, "Codrituzumab directed to patients with locally advanced or metastatic hepatocellular cancer (Anti-Glypcan-3 Monoclonal Antibody), an open-circuit multiple facility for the combination of Atezolizumab and the first phase dose escalation test," JapicCTI-No. JapicCTI-163325 (2017).

Japanese Office Action dated Oct. 4, 2022 in Japanese Patent Application No. 2020-516764.

* cited by examiner

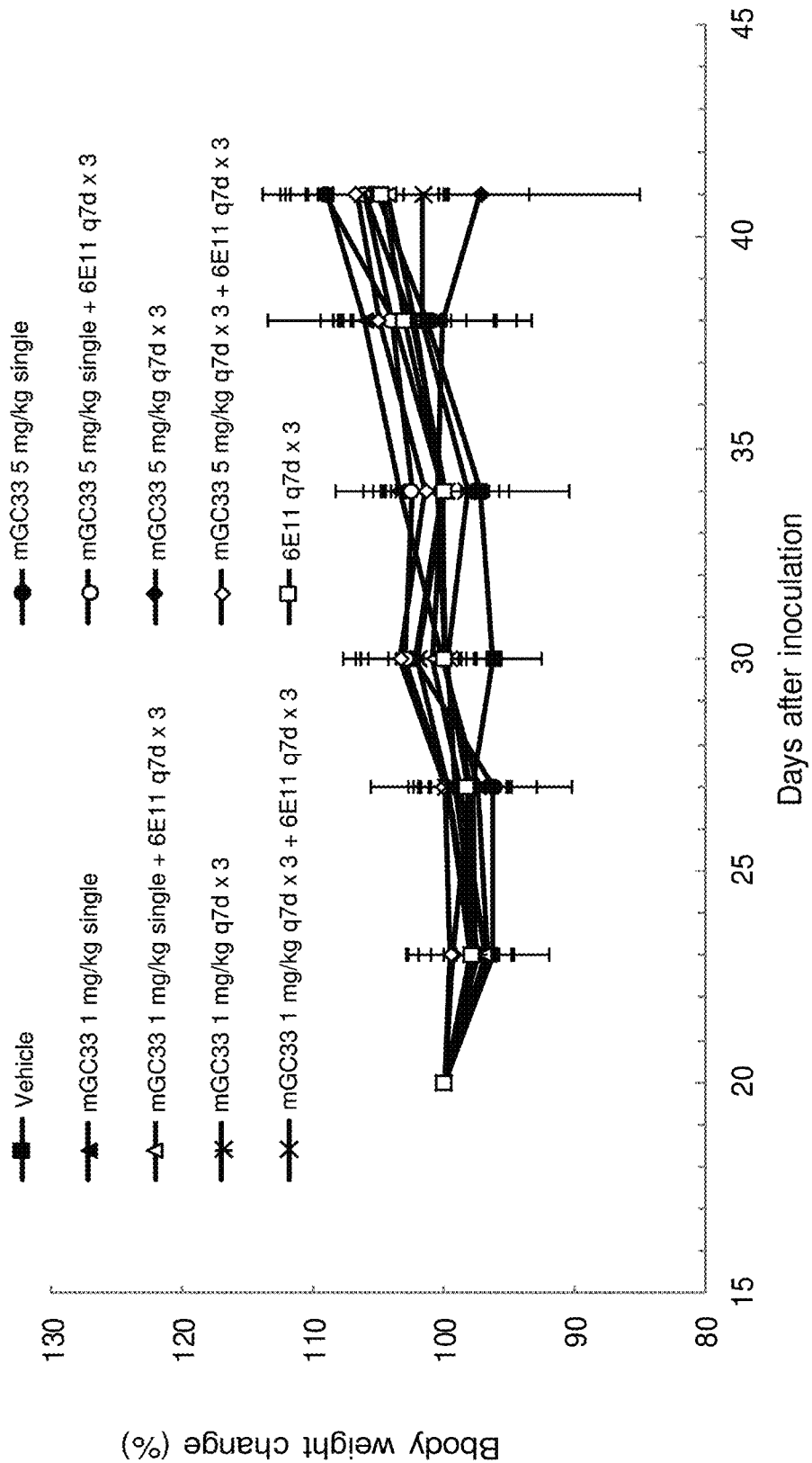

METHODS OF TREATING CANCERS USING PD-1 AXIS BINDING ANTAGONISTS AND ANTI-GPC3 ANTIBODIES

CROSS-REFERENCE TO RELATED APPLICATIONS

This application is a U.S. National Phase of PCT Application No. PCT/JP2017/010267, filed Mar. 14, 2017, which claims priority to Japanese Patent Application No. 2016-051424, filed Mar. 15, 2016, each of which is incorporated herein by reference.

REFERENCE TO SEQUENCE LISTING SUBMITTED ELECTRONICALLY

The content of the electronically submitted sequence listing (Name: 6663_0100_Sequence_Listing.txt; Size: 36.4 kilobytes; and Date of Creation: Sep. 11, 2018) filed with the application is incorporated herein by reference in its entirety.

FIELD OF THE INVENTION

This invention relates to methods of treating cancers by administering a PD-1 axis binding antagonist and an anti-GPC3 antibody.

BACKGROUND OF THE INVENTION

Hepatocellular cancer is reportedly the fifth leading cause of cancer deaths worldwide, accounting for approximately 600,000 deaths each year (Non Patent Literature 1). Most patients with hepatocellular cancer die within 1 year after being diagnosed with the disease. Unfortunately, hepatocellular cancer cases are frequently diagnosed at a late stage which rarely responds to curative therapies. Still, medical treatments including chemotherapy, chemoembolization, ablation, and proton beam therapy are insufficiently effective for such patients. Many patients exhibit recurrence of the disease with vascular invasion and multiple intrahepatic metastases, which rapidly progresses to the advanced stage. Their 5-year survival rates are only 7% (Non Patent Literature 2). Patients with hepatocellular cancer amenable to the resection of local foci have relatively good prognosis, though their 5-year survival rates still remain at a level of 15% and 39% (Non Patent Literature 3). Thus, there has been a demand in the art for novel therapy for such a malignant disease hepatocellular cancer.

Hepatocellular cancer is reportedly responsible for more than 90% of primary liver cancer cases in Japan. Medical methods for treating such hepatocellular cancer include, for example, chemotherapy-based transcatheter arterial embolization (TAE) therapy, which involves inducing the selective necrosis of the hepatocellular cancer by the injection of a mixture of an oil-based contrast medium (Lipiodol), an anticancer agent, and an obstructing substance (Gelfoam) into the hepatic artery (which serves as a nutrient supply pathway to the tumor) resulting in the obstruction of the nutrient artery. In addition, invasive approaches are used, such as percutaneous ethanol injection, percutaneous microwave coagulation therapy, and radiofrequency ablation. Also, clinical trials have been conducted on systemic chemotherapy using chemotherapeutic agents such as fluorouracil (5-FU), uracil-tegafur (UFT), mitomycin C (MMC), mitoxantrone (DHAD), adriamycin (ADR), epirubicin (EPI), and cisplatin (CDDP) either alone or in combination with interferon (IFN) (Non Patent Literature 4).

Meanwhile, an orally active form of sorafenib (Nexavar, BAY43-9006) has been approved, which is more advantageously effective than the chemotherapeutic agents described above in such a way that this agent blocks the growth of cancer cells by inhibiting Raf kinase in the Raf/MEK/ERK signal transduction while the agent exerts antiangiogenic effects by targeting VEGFR-2, VEGFR-3, and PDGFR-.beta. tyrosine kinases. The efficacy of sorafenib has been studied in two phase-III multicenter placebo-controlled trials (Sorafenib HCC Assessment Randomized Protocol (SHARP) trial and Asia-Pacific trial) targeting advanced hepatocellular cancer. Sorafenib was confirmed to prolong survival durations, with HR of 0.68, in both of these trials. In the SHARP trial, sorafenib prolonged the survival duration to 10.7 months versus 7.9 months with the placebo. In the Asian trial, this agent prolonged the survival duration to 6.5 months versus 4.2 months with the placebo. The agent, however, had a low objective response rate and showed no prolongation of a time to symptomatic progression, though the agent prolonged a time to tumor progression (5.5 months versus 2.8 months in the European and American trial and 2.8 months versus 1.4 months in the Asian trial) on the images. The Asian cohorts exhibited a short duration of life prolongation, which is probably because their treatments were started at a slightly later stage during the disease process in the Asian region compared with Europe and the United States (Non Patent Literatures 5 and 6).

As liver cancer progresses, its specific symptoms associated with liver dysfunction are generally observed, such as anorexia, weight loss, general malaise, palpable right hypochondrial mass, right hypochondrial pain, sense of abdominal fullness, fever, and jaundice. The chemotherapeutic agents (e.g., sorafenib), however, have complications to be overcome, including their inherent adverse reactions such as diarrhea or constipation, anemia, suppression of the immune system to cause infection or sepsis (with lethal severity), hemorrhage, cardiac toxicity, hepatic toxicity, renal toxicity, anorexia, and weight loss.

Although particular early-stage symptoms are not initially observed in liver cancer, its specific symptoms associated with liver dysfunction, such as anorexia, weight loss, general malaise, palpable right hypochondrial mass, right hypochondrial pain, sense of abdominal fullness, fever, and jaundice, are generally observed with progression of the liver cancer. According to clinical observation, such symptoms are enhanced by use of the chemotherapeutic agents. For example, anorexia in a patient with detectable liver cancer cells and symptoms such as weight loss associated with or independent of the anorexia may be more enhanced by the administration of the chemotherapeutic agents to the patient than without the use of the chemotherapeutic agents. In some cases, the use of the chemotherapeutic agents must be discontinued for the patient having such symptoms. These enhanced symptoms are impediments to treatments with the chemotherapeutic agents. Thus, there has been a demand for the establishment of excellent therapy from the viewpoint of, for example, improving therapeutic effects or improving QOL of patients to be treated.

Glypican 3 (GPC3) is frequently expressed at a high level in liver cancer and as such, seems to be useful in the identification of its functions in liver cancer or as a therapeutic or diagnostic target of liver cancer.

Under the circumstances described above, drugs are under development with GPC3 as a therapeutic target of liver cancer. A liver cancer drug comprising an anti-GPC3 antibody as an active ingredient has been developed, the antibody having antibody-dependent cellular cytotoxicity (hereinafter, referred to as "ADCC") activity and/or complement-dependent cytotoxicity (hereinafter, referred to as "CDC") activity against cells expressing GPC3 (Patent Literature 1). Also, a GPC3-targeting drug comprising a humanized anti-GPC3 antibody having ADCC activity and CDC activity as an active ingredient has been developed (Patent Literature 2). Further GPC3-targeting drugs have been developed, which comprise a humanized anti-GPC3 antibody with enhanced ADCC activity (Patent Literatures 3 and 4) or an anti-GPC3 antibody having ADCC activity and CDC activity as well as improved plasma dynamics (Patent Literature 5). These anti-GPC3 antibodies in combination therapy with the chemotherapeutic agents such as sorafenib have been found to attenuate the adverse reactions, for example, brought about by the sole therapy of the chemotherapeutic agents (e.g., sorafenib) and also found to exhibit synergistic effects based on these agents (Patent Literature 6). Accordingly, excellent methods for treating liver cancer are in the process of being established using GPC3-targeting drugs as the nucleus from the viewpoint of, for example, improving therapeutic effects or improving QOL of patients to be treated.

On the other hand, The provision of two distinct signals to T-cells is a widely accepted model for lymphocyte activation of resting T lymphocytes by antigen-presenting cells (APCs). Lafferty et al, Aust. J. Exp. Biol. Med. Sci 53: 27-42 (1975). This model further provides for the discrimination of self from non-self and immune tolerance. Bretscher et al, Science 169: 1042-1049 (1970); Bretscher, P. A., Proc. Nat. Acad. Sci. USA 96: 185-190 (1999); Jenkins et al, J. Exp. Med. 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), inducing T-cells to promote clonal expansion, cytokine secretion and effector function. Lenschow et al., Ann. Rev. Immunol. 14:233 (1996). In the absence of co-stimulation, T-cells can become refractory to antigen stimulation, do not mount an effective immune response, and further may result in exhaustion or tolerance to foreign antigens.

In the two-signal model T-cells receive both positive and negative secondary co-stimulatory signals. The regulation of such positive and negative signals is critical to maximize the host's protective immune responses, while maintaining immune tolerance and preventing autoimmunity. Negative secondary signals seem necessary for induction of T-cell tolerance, while positive signals promote T-cell activation. While the simple two-signal model still provides a valid explanation for naïve lymphocytes, a host's immune response is a dynamic process, and co-stimulatory signals can also be provided to antigen-exposed T-cells. The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting of PD-1 and other molecules which signal through interactions with PD-1, such as programmed death ligand 1 (PD-L1) and programmed death ligand 2 (PD-L2) are an area of intense interest.

PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8): 1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction may enhance CD8+ T cell-mediated killing of tumors.

Therapeutic targeting PD-1 and other molecules which signal through interactions with PD-1, such as programmed death ligand 1 (PD-L1) and programmed death ligand 2 (PD-L2) are an area of intense interest. The inhibition of PD-L1 signaling has been proposed as a means to enhance T cell immunity for the treatment of cancer (e.g., tumor immunity) and infection, including both acute and chronic (e.g., persistent) infection. An optimal therapeutic treatment may combine blockade of PD-1 receptor/ligand interaction with an agent that directly inhibits tumor growth. There remains a need for an optimal therapy for treating, stabilizing, preventing, and/or delaying development of various cancers.

All references cited herein, including patent applications, patent publications, and UniProtKB/Swiss-Prot Accession numbers are herein incorporated by reference in their entirety, as if each individual reference were specifically and individually indicated to be incorporated by reference.

The Present Invention Provides:
[1] A pharmaceutical composition for treating or delaying progression of cancer in an individual for use in combination with a PD-1 axis binding antagonist, said composition comprising an anti-GPC3 antibody as an active ingredient.
[2] The pharmaceutical composition according to [1], wherein the anti-GPC3 antibody is administered before administration of the PD-1 axis binding antagonist, simultaneous with administration of the PD-1 axis binding antagonist, or after administration of the PD-1 axis binding antagonist.
[3] The pharmaceutical composition according to [1] or [2], wherein the PD-1 axis binding antagonist is selected from the group consisting of a PD-1 binding antagonist, a PD-L1 binding antagonist and a PD-L2 binding antagonist.
[4] The pharmaceutical composition according to [3], wherein the PD-1 axis binding antagonist is a PD-1 binding antagonist.
[5] The pharmaceutical composition according to [4], wherein the PD-1 binding antagonist inhibits the binding of PD-1 to its ligand binding partners.
[6] The pharmaceutical composition according to [5], wherein the PD-1 binding antagonist inhibits the binding of PD-1 to PD-L1.
[7] The pharmaceutical composition according to [5], wherein the PD-1 binding antagonist inhibits the binding of PD-1 to PD-L2.
[8] The pharmaceutical composition according to [5], wherein the PD-1 binding antagonist inhibits the binding of PD-1 to both PD-L1 and PD-L2.

[9] The pharmaceutical composition according to [5], wherein the PD-1 binding antagonist is an antibody.

[10] The pharmaceutical composition according to [5], wherein the PD-1 binding antagonist is selected from the group consisting of nivolumab, lambrolizumab (pembrolizumab), and pidilizumab.

[11] The pharmaceutical composition according to [2], wherein the PD-1 axis binding antagonist is a PD-L1 binding antagonist.

[12] The pharmaceutical composition according to [11], wherein the PD-L1 binding antagonist inhibits the binding of PD-L1 to PD-1.

[13] The pharmaceutical composition according to [11], wherein the PD-L1 binding antagonist inhibits the binding of PD-L1 to B7-1.

[14] The pharmaceutical composition according to [11], wherein the PD-L1 binding antagonist inhibits the binding of PD-L1 to both PD-1 and B7-1.

[15] The pharmaceutical composition according to any one of [12] to [14], wherein the PD-L1 binding antagonist is an anti-PD-L1 antibody.

[16] The pharmaceutical composition according to [11], wherein the PD-L1 binding antagonist is selected from the group consisting of: YW243.55.S70, Atezolizumab, MPDL3280A, MDX-1105, avelumab, and MEDI4736 (durvalumab).

[17] The pharmaceutical composition according to [15], wherein the anti-PD-L1 antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24.

[18] The pharmaceutical composition according to [15], wherein the anti-PD-L1 antibody comprises a heavy chain variable region comprising the amino acid sequence of SEQ ID NO:25 or 26 and a light chain variable region comprising the amino acid sequence of SEQ ID NO:4.

[19] The pharmaceutical composition according to [3], wherein the PD-1 axis binding antagonist is a PD-L2 binding antagonist.

[20] The pharmaceutical composition according to [19], wherein the PD-L2 binding antagonist is an antibody.

[21] The pharmaceutical composition according to [19], wherein the PD-L2 binding antagonist is an immunoadhesin.

[22] The pharmaceutical composition according to any one of [1] to [21], wherein the anti-GPC3 antibody comprises a heavy chain comprising HVR-H1 sequence of SEQ ID NO:34, HVR-H2 sequence of SEQ ID NO:35, and HVR-H3 sequence of SEQ ID NO:36; and a light chain comprising HVR-L1 sequence of SEQ ID NO:37, HVR-L2 sequence of SEQ ID NO:38, and HVR-L3 sequence of SEQ ID NO:39.

[23] The pharmaceutical composition according to any one of [1] to [21], wherein the anti-GPC3 antibody is capable of binding to an epitope to which a second antibody can bind, wherein said second antibody comprises a heavy chain comprising HVR-H1 sequence of SEQ ID NO:42, HVR-H2 sequence of SEQ ID NO:43, and HVR-H3 sequence of SEQ ID NO:44; and a light chain comprising HVR-L1 sequence of SEQ ID NO:45, HVR-L2 sequence of SEQ ID NO:46, and HVR-L3 sequence of SEQ ID NO:47.

[24] The pharmaceutical composition according to any one of [1] to [23] wherein the anti-GPC3 antibody is a humanized antibody.

[25] The pharmaceutical composition according to [24], wherein the anti-GPC3 antibody comprises a heavy chain variable region comprising the amino acid sequence of SEQ ID NO:50 and a light chain variable region comprising the amino acid sequence of SEQ ID NO:52.

[26] The pharmaceutical composition according to any one of [1] to [25], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[27] A pharmaceutical composition for treating or delaying progression of cancer in an individual for use in combination with an anti-GPC3 antibody, said composition comprising a PD-1 axis binding antagonist as an active ingredient.

[28] The pharmaceutical composition according to [27], wherein the anti-GPC3 antibody is administered before administration of the PD-1 axis binding antagonist, simultaneous with administration of the PD-1 axis binding antagonist, or after administration of the PD-1 axis binding antagonist.

[29] The pharmaceutical composition according to [27] or [28], wherein the PD-1 axis binding antagonist is selected from the group consisting of a PD-1 binding antagonist, a PD-L1 binding antagonist and a PD-L2 binding antagonist.

[30] The pharmaceutical composition according to [29], wherein the PD-1 axis binding antagonist is a PD-1 binding antagonist.

[31] The pharmaceutical composition according to [30], wherein the PD-1 binding antagonist inhibits the binding of PD-1 to its ligand binding partners.

[32] The pharmaceutical composition according to [31], wherein the PD-1 binding antagonist inhibits the binding of PD-1 to PD-L1.

[33] The pharmaceutical composition according to [31], wherein the PD-1 binding antagonist inhibits the binding of PD-1 to PD-L2.

[34] The pharmaceutical composition according to [31], wherein the PD-1 binding antagonist inhibits the binding of PD-1 to both PD-L1 and PD-L2.

[35] The pharmaceutical composition according to [31], wherein the PD-1 binding antagonist is an antibody.

[36] The pharmaceutical composition according to [31], wherein the PD-1 binding antagonist is selected from the group consisting of nivolumab, lambrolizumab (pembrolizumab), and pidilizumab.

[37] The pharmaceutical composition according to [28], wherein the PD-1 axis binding antagonist is a PD-L1 binding antagonist.

[38] The pharmaceutical composition according to [37], wherein the PD-L1 binding antagonist inhibits the binding of PD-L1 to PD-1.

[39] The pharmaceutical composition according to [37], wherein the PD-L1 binding antagonist inhibits the binding of PD-L1 to B7-1.

[40] The pharmaceutical composition according to [37], wherein the PD-L1 binding antagonist inhibits the binding of PD-L1 to both PD-1 and B7-1.

[41] The pharmaceutical composition according to any one of [38] to [40], wherein the PD-L1 binding antagonist is an anti-PD-L1 antibody.

[42] The pharmaceutical composition according to [37], wherein the PD-L1 binding antagonist is selected from the group consisting of: YW243.55.S70, Atezolizumab, MPDL3280A, MDX-1105, avelumab, and MEDI4736 (durvalumab).

[43] The pharmaceutical composition according to [41], wherein the anti-PD-L1 antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24.

[44] The pharmaceutical composition according to [41], wherein the anti-PD-L1 antibody comprises a heavy chain variable region comprising the amino acid sequence of SEQ ID NO:25 or 26 and a light chain variable region comprising the amino acid sequence of SEQ ID NO:4.

[45] The pharmaceutical composition according to [29], wherein the PD-1 axis binding antagonist is a PD-L2 binding antagonist.

[46] The pharmaceutical composition according to [45], wherein the PD-L2 binding antagonist is an antibody.

[47] The pharmaceutical composition according to [45], wherein the PD-L2 binding antagonist is an immunoadhesin.

[48] The pharmaceutical composition according to any one of [27] to [47], wherein the anti-GPC3 antibody comprises a heavy chain comprising HVR-H1 sequence of SEQ ID NO:34, HVR-H2 sequence of SEQ ID NO:35, and HVR-H3 sequence of SEQ ID NO:36; and a light chain comprising HVR-L1 sequence of SEQ ID NO:37, HVR-L2 sequence of SEQ ID NO:38, and HVR-L3 sequence of SEQ ID NO:39.

[49] The pharmaceutical composition according to any one of [27] to [47], wherein the anti-GPC3 antibody is capable of binding to an epitope to which a second antibody can bind, wherein said second antibody comprises a heavy chain comprising HVR-H1 sequence of SEQ ID NO:42, HVR-H2 sequence of SEQ ID NO:43, and HVR-H3 sequence of SEQ ID NO:44; and a light chain comprising HVR-L1 sequence of SEQ ID NO:45, HVR-L2 sequence of SEQ ID NO:46, and HVR-L3 sequence of SEQ ID NO:47.

[50] The pharmaceutical composition according to any one of [27] to [49] wherein the anti-GPC3 antibody is a humanized antibody.

[51] The pharmaceutical composition according to [50], wherein the anti-GPC3 antibody comprises a heavy chain variable region comprising the amino acid sequence of SEQ ID NO:50 and a light chain variable region comprising the amino acid sequence of SEQ ID NO:52.

[52] The pharmaceutical composition according to any one of [27] to [51], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[53] A pharmaceutical composition for treating or delaying progression of cancer in an individual comprising a combination of a PD-1 axis binding antagonist and an anti-GPC3 antibody as an active ingredient.

[54] The pharmaceutical composition according to [53], wherein the pharmaceutical composition is a combination preparation.

[55] The pharmaceutical composition according to [53], wherein the anti-GPC3 antibody is administered before administration of the PD-1 axis binding antagonist, simultaneous with administration of the PD-1 axis binding antagonist, or after administration of the PD-1 axis binding antagonist.

[56] The pharmaceutical composition according to [53] or [55], wherein the PD-1 axis binding antagonist is selected from the group consisting of a PD-1 binding antagonist, a PD-L1 binding antagonist and a PD-L2 binding antagonist.

[57] The pharmaceutical composition according to [56], wherein the PD-1 axis binding antagonist is a PD-1 binding antagonist.

[58] The pharmaceutical composition according to [57], wherein the PD-1 binding antagonist inhibits the binding of PD-1 to its ligand binding partners.

[59] The pharmaceutical composition according to [58], wherein the PD-1 binding antagonist inhibits the binding of PD-1 to PD-L1.

[60] The pharmaceutical composition according to [58], wherein the PD-1 binding antagonist inhibits the binding of PD-1 to PD-L2.

[61] The pharmaceutical composition according to [58], wherein the PD-1 binding antagonist inhibits the binding of PD-1 to both PD-L1 and PD-L2.

[62] The pharmaceutical composition according to [58], wherein the PD-1 binding antagonist is an antibody.

[63] The pharmaceutical composition according to [58], wherein the PD-1 binding antagonist is selected from the group consisting of nivolumab, lambrolizumab (pembrolizumab), and pidilizumab.

[64] The pharmaceutical composition according to [55], wherein the PD-1 axis binding antagonist is a PD-L1 binding antagonist.

[65] The pharmaceutical composition according to [64], wherein the PD-L1 binding antagonist inhibits the binding of PD-L1 to PD-1.

[66] The pharmaceutical composition according to [64], wherein the PD-L1 binding antagonist inhibits the binding of PD-L1 to B7-1.

[67] The pharmaceutical composition according to [64], wherein the PD-L1 binding antagonist inhibits the binding of PD-L1 to both PD-1 and B7-1.

[68] The pharmaceutical composition according to any one of [65] to [67], wherein the PD-L1 binding antagonist is an anti-PD-L1 antibody.

[69] The pharmaceutical composition according to [64], wherein the PD-L1 binding antagonist is selected from the group consisting of: YW243.55.S70, Atezolizumab, MPDL3280A, MDX-1105, avelumab, and MEDI4736 (durvalumab).

[70] The pharmaceutical composition according to [68], wherein the anti-PD-L1 antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24.

[71] The pharmaceutical composition according to [68], wherein the anti-PD-L1 antibody comprises a heavy chain variable region comprising the amino acid sequence of SEQ ID NO:25 or 26 and a light chain variable region comprising the amino acid sequence of SEQ ID NO:4.

[72] The pharmaceutical composition according to [56], wherein the PD-1 axis binding antagonist is a PD-L2 binding antagonist.

[73] The pharmaceutical composition according to [72], wherein the PD-L2 binding antagonist is an antibody.

[74] The pharmaceutical composition according to [72], wherein the PD-L2 binding antagonist is an immunoadhesin.

[75] The pharmaceutical composition according to any one of [53] to [74], wherein the anti-GPC3 antibody comprises a heavy chain comprising HVR-H1 sequence of SEQ ID NO:34, HVR-H2 sequence of SEQ ID NO:35, and HVR-H3 sequence of SEQ ID NO:36; and a light chain comprising HVR-L1 sequence of SEQ ID NO:37, HVR-L2 sequence of SEQ ID NO:38, and HVR-L3 sequence of SEQ ID NO:39.

[76] The pharmaceutical composition according to any one of [53] to [74], wherein the anti-GPC3 antibody is capable of binding to an epitope to which a second antibody can bind, wherein said second antibody comprises a heavy chain comprising HVR-H1 sequence of SEQ ID NO:42, HVR-H2 sequence of SEQ ID NO:43, and HVR-H3 sequence of SEQ ID NO:44; and a light chain comprising HVR-L1 sequence of SEQ ID NO:45, HVR-L2 sequence of SEQ ID NO:46, and HVR-L3 sequence of SEQ ID NO:47.

[77] The pharmaceutical composition according to any one of [53] to [76] wherein the anti-GPC3 antibody is a humanized antibody.

[78] The pharmaceutical composition according to [77], wherein the anti-GPC3 antibody comprises a heavy chain variable region comprising the amino acid sequence of SEQ ID NO:50 and a light chain variable region comprising the amino acid sequence of SEQ ID NO:52.

[79] The pharmaceutical composition according to any one of [53] to [78], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[80] A pharmaceutical composition for enhancing immune responses against tumor cells in individual for use in combination with a PD-1 axis binding antagonist, said composition comprising an anti-GPC3 antibody as an active ingredient.

[81] A pharmaceutical composition for enhancing immune responses against tumor cells in individual for use in combination with an anti-GPC3 antibody, said composition comprising a PD-1 axis binding antagonist as an active ingredient.

[82] A pharmaceutical composition for enhancing immune responses against tumor cells in individual comprising a combination of a PD-1 axis binding antagonist and an anti-GPC3 antibody as an active ingredient.

[83] The pharmaceutical composition according to any one of [80] to [82], wherein the anti-GPC3 antibody is administered before administration of the PD-1 axis binding antagonist, simultaneous with administration of the PD-1 axis binding antagonist, or after administration of the PD-1 axis binding antagonist.

[84] The pharmaceutical composition according to any one of [80] to [83], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[85] A method for treating or delaying progression of cancer in an individual comprising administering to the individual an effective amount of a PD-1 axis binding antagonist and an anti-GPC3 antibody.

[86] The method according to [85], wherein the anti-GPC3 antibody is administered before administration of the PD-1 axis binding antagonist, simultaneous with administration of the PD-1 axis binding antagonist, or after administration of the PD-1 axis binding antagonist.

[87] The method according to [85] or [86], wherein the PD-1 axis binding antagonist is selected from the group consisting of a PD-1 binding antagonist, a PD-L1 binding antagonist and a PD-L2 binding antagonist.

[88] The method according to [87], wherein the PD-1 axis binding antagonist is a PD-1 binding antagonist.

[89] The method according to [88], wherein the PD-1 binding antagonist inhibits the binding of PD-1 to its ligand binding partners.

[90] The method according to [89], wherein the PD-1 binding antagonist inhibits the binding of PD-1 to PD-L1.

[91] The method according to [89], wherein the PD-1 binding antagonist inhibits the binding of PD-1 to PD-L2.

[92] The method according to [89], wherein the PD-1 binding antagonist inhibits the binding of PD-1 to both PD-L1 and PD-L2.

[93] The method according to [89], wherein the PD-1 binding antagonist is an antibody.

[94] The method according to [89], wherein the PD-1 binding antagonist is selected from the group consisting of nivolumab, lambrolizumab (pembrolizumab), and pidilizumab.

[95] The method according to [81], wherein the PD-1 axis binding antagonist is a PD-L1 binding antagonist.

[96] The method according to [95], wherein the PD-L1 binding antagonist inhibits the binding of PD-L1 to PD-1.

[97] The method according to [95], wherein the PD-L1 binding antagonist inhibits the binding of PD-L1 to B7-1.

[98] The method according to [95], wherein the PD-L1 binding antagonist inhibits the binding of PD-L1 to both PD-1 and B7-1.

[99] The method according to any one of [96] to [98], wherein the PD-L1 binding antagonist is an anti-PD-L1 antibody.

[100] The method according to [95], wherein the PD-L1 binding antagonist is selected from the group consisting of: YW243.55.S70, Atezolizumab, MPDL3280A, MDX-1105, avelumab, and MEDI4736(durvalumab).

[101] The method according to [99], wherein the anti-PD-L1 antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24.

[102] The method according to [99], wherein the anti-PD-L1 antibody comprises a heavy chain variable region comprising the amino acid sequence of SEQ ID NO:25 or 26 and a light chain variable region comprising the amino acid sequence of SEQ ID NO:4.

[103] The method according to [87], wherein the PD-1 axis binding antagonist is a PD-L2 binding antagonist.

[104] The method according to [103], wherein the PD-L2 binding antagonist is an antibody.

[105] The method according to [103], wherein the PD-L2 binding antagonist is an immunoadhesin.

[106] The method according to any one of [85] to [105], wherein the anti-GPC3 antibody comprises a heavy chain comprising HVR-H1 sequence of SEQ ID NO:34, HVR-H2 sequence of SEQ ID NO:35, and HVR-H3 sequence of SEQ ID NO:36; and a light chain comprising HVR-L1 sequence of SEQ ID NO:37, HVR-L2 sequence of SEQ ID NO:38, and HVR-L3 sequence of SEQ ID NO:39.

[107] The method according to any one of [85] to [105], wherein the anti-GPC3 antibody is capable of binding to an epitope to which a second antibody can bind, wherein said second antibody comprises a heavy chain comprising HVR-H1 sequence of SEQ ID NO:42, HVR-H2 sequence of SEQ ID NO:43, and HVR-H3 sequence of SEQ ID NO:44; and a light chain comprising HVR-L1 sequence of SEQ ID NO:45, HVR-L2 sequence of SEQ ID NO:46, and HVR-L3 sequence of SEQ ID NO:47.

[108] The method according to any one of [85] to [107] wherein the anti-GPC3 antibody is a humanized antibody.

[109] The method according to [108], wherein the anti-GPC3 antibody comprises a heavy chain variable region comprising the amino acid sequence of SEQ ID NO:50 and a light chain variable region comprising the amino acid sequence of SEQ ID NO:52.

[110] The method according to any one of [85] to [109], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[111] A method for enhancing immune responses against tumor cells in individual for use in combination with a PD-1 axis binding antagonist, said composition comprising an anti-GPC3 antibody as an active ingredient.

[112] A method for enhancing immune responses against tumor cells in individual for use in combination with an anti-GPC3 antibody, said composition comprising a PD-1 axis binding antagonist as an active ingredient.

[113] A method for enhancing immune responses against tumor cells in individual comprising a combination of a PD-1 axis binding antagonist and an anti-GPC3 antibody as an active ingredient.

[114] The method according to any one of [111] to [113], wherein the anti-GPC3 antibody is administered before administration of the PD-1 axis binding antagonist, simultaneous with administration of the PD-1 axis binding antagonist, or after administration of the PD-1 axis binding antagonist.

[115] The method composition according to any one of [111] to [114], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[116] A combination for treating or delaying progression of cancer in an individual comprising a PD-1 axis binding antagonist and an anti-GPC3 antibody.

[117] The combination according to [116], wherein the anti-GPC3 antibody is administered before administration of the PD-1 axis binding antagonist, simultaneous with administration of the PD-1 axis binding antagonist, or after administration of the PD-1 axis binding antagonist.

[118] The combination according to [116] or [117], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[119] A kit comprising
   (1) a pharmaceutical composition comprising an anti-GPC3 antibody as an active ingredient,
   (2) a container and
   (3) a package insert or label comprising instructions for administration of the pharmaceutical composition in combination with a PD-1 axis binding antagonist for treating or delaying progression of a cancer in an individual.

[120] A kit comprising a first pharmaceutical composition comprising a PD-1 axis binding antagonist as an active ingredient and a second pharmaceutical composition comprising an anti-GPC3 antibody as an active ingredient.

[121] The kit according to [119] or [120], wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

The Present Invention Also Provides:

[122] Use of a PD-1 axis binding antagonist in the manufacture of a medicament for treating or delaying progression of cancer in an individual, wherein the medicament comprises the PD-1 axis binding antagonist and an optional pharmaceutically acceptable carrier, and wherein the treatment comprises administration of the medicament in combination with a composition comprising an anti-GPC3 antibody and an optional pharmaceutically acceptable carrier.

[123] Use of an anti-GPC3 antibody in the manufacture of a medicament for treating or delaying progression of cancer in an individual, wherein the medicament comprises the anti-GPC3 antibody and an optional pharmaceutically acceptable carrier, and wherein the treatment comprises administration of the medicament in combination with a composition comprising a PD-1 axis binding antagonist and an optional pharmaceutically acceptable carrier.

SUMMARY OF THE INVENTION

The inventors have discovered that by combining an anti-GPC3 antibody with a human PD-1 axis binding antagonist, better therapeutic effects can be achieved in a cancer patient than when such an anti-GPC3 antibody or a human PD-1 axis binding antagonist is used alone.

In one aspect, provided herein is a method for treating or delaying progression of cancer in an individual comprising administering to the individual an effective amount of a human PD-1 axis binding antagonist and an anti-GPC3 antibody.

In another aspect, provided herein is a method of enhancing immune responses against tumor cells in an individual having cancer comprising administering an effective amount of a PD-1 axis binding antagonist and an anti-GPC3 antibody. For example, enhanced immune responses against tumor cells includes infiltration of immune cells including macrophages and multinucleated giant cells in to tumor tissues. For another example, enhanced immune responses against tumor cells includes increase of CD45-positive lymphocytes, CD3ε-positive lymphocytes and CD8-positive T lymphocytes in tumor infiltrated lymphocytes (TILs).

In another aspect, provided herein is use of a human PD-1 axis binding antagonist in the manufacture of a medicament for treating or delaying progression of cancer in an individual, wherein the medicament comprises the human PD-1 axis binding antagonist and an optional pharmaceutically acceptable carrier, and wherein the treatment comprises administration of the medicament in combination with a composition comprising an anti-GPC3 antibody and an optional pharmaceutically acceptable carrier.

In another aspect, provided herein is use of an anti-GPC3 antibody in the manufacture of a medicament for treating or delaying progression of cancer in an individual, wherein the medicament comprises the anti-GPC3 antibody and an optional pharmaceutically acceptable carrier, and wherein the treatment comprises administration of the medicament in combination with a composition comprising a human PD-1 axis binding antagonist and an optional pharmaceutically acceptable carrier.

In another aspect, provided herein is a composition comprising a human PD-1 axis binding antagonist and an optional pharmaceutically acceptable carrier for use in treating or delaying progression of cancer in an individual, wherein the treatment comprises administration of said composition in combination with a second composition, wherein the second composition comprises an anti-GPC3 antibody and an optional pharmaceutically acceptable carrier.

In another aspect, provided herein is a composition comprising an anti-GPC3 antibody and an optional pharmaceutically acceptable carrier for use in treating or delaying progression of cancer in an individual, wherein the treatment comprises administration of said composition in combination with a second composition, wherein the second composition comprises a human PD-1 axis binding antagonist and an optional pharmaceutically acceptable carrier.

In another aspect, provided herein is a kit comprising a medicament comprising a PD-1 axis binding antagonist and an optional pharmaceutically acceptable carrier, and a package insert comprising instructions for administration of the medicament in combination with a composition comprising an anti-GPC3 antibody and an optional pharmaceutically acceptable carrier for treating or delaying progression of cancer in an individual.

In another aspect, provided herein is a kit comprising a first medicament comprising a PD-1 axis binding antagonist and an optional pharmaceutically acceptable carrier, and a second medicament comprising an anti-GPC3 antibody and an optional pharmaceutically acceptable carrier. In some embodiments, the kit further comprises a package insert comprising instructions for administration of the first medicament and the second medicament for treating or delaying progression of cancer in an individual.

In another aspect, provided herein is a kit comprising a medicament comprising an anti-GPC3 antibody and an optional pharmaceutically acceptable carrier, and a package insert comprising instructions for administration of the medicament in combination with a composition comprising a PD-1 axis binding antagonist and an optional pharmaceutically acceptable carrier for treating or delaying progression of cancer in an individual.

In some embodiments of the methods, uses, compositions, and kits described above and herein, the PD-1 axis binding antagonist is selected from the group consisting of a PD-1 binding antagonist, a PD-L1 binding antagonist and a PD-L2 binding antagonist. In some embodiments, the PD-1 axis binding antagonist is an antibody. In some embodiments, the antibody is a humanized antibody, a chimeric antibody or a human antibody. In some embodiments, the antibody is an antigen binding fragment. In some embodiments, the antigen-binding fragment is selected from the group consisting of Fab, Fab', F(ab')2, scFv and Fv.

In some embodiments, the PD-1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an antibody. In some embodiments, the PD-1 binding antagonist is selected from the group consisting of MDX-1106 (nivolumab), MK-3475 (pembrolizumab, lambrolizumab), CT-011 (pidilizumab), PDR001, REGN2810, BGB A317, SHR-1210, AMP-514 (MEDI0680), and AMP-224.

In some embodiments, the PD-1 axis binding antagonist is a PD-L1 binding antagonist. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an antibody. In some embodiments, the PD-L1 binding antagonist is selected from the group consisting of: YW243.55.S70, Atezolizumab, MPDL3280A, MDX-1105, avelumab, and MEDI4736 (durvalumab). In some embodiments, the anti-PD-L1 antibody comprises a heavy chain comprising HVR-H1 sequence of SEQ ID NO:19, HVR-H2 sequence of SEQ ID NO:20, and HVR-H3 sequence of SEQ ID NO:21; and/or a light chain comprising HVR-L1 sequence of SEQ ID NO:22, HVR-L2 sequence of SEQ ID NO:23, and HVR-L3 sequence of SEQ ID NO:24. In some embodiment, the anti-PD-L1 antibody comprises a heavy chain variable region comprising the amino acid sequence of SEQ ID NO:25 or 26 and/or a light chain variable region comprising the amino acid sequence of SEQ ID NO:4. In some embodiments, the anti-PD-L1 antibody comprises the three heavy chain HVR sequences of antibody YW243.55.570 and/or the three light chain HVR sequences of antibody YW243.55.570 described in WO2010/077634 and U.S. Pat. No. 8,217,149, which are incorporated herein by reference. In some embodiments, the anti-PD-L1 antibody comprises the heavy chain variable region sequence of antibody YW243.55.S70 and/or the light chain variable region sequence of antibody YW243.55.570. In some embodiments, the anti-PD-L1 antibody is Atezolizumab.

In some embodiments, the PD-1 axis binding antagonist is a PD-L2 binding antagonist. In some embodiments, the PD-L2 binding antagonist is an antibody. In some embodiments, the PD-L2 binding antagonist is an immunoadhesion.

In some embodiments of the methods, uses, compositions, and kits described above and herein, the anti-GPC3 antibody is a humanized antibody, a chimeric antibody or a human antibody. In some embodiments, the antibody is an antigen binding fragment. In some embodiments, the antigen-binding fragment is selected from the group consisting of Fab, Fab', F(ab')2, scFv and Fv.

In some embodiments, the anti-GPC3 antibody is GC33 or codrituzumab. In some embodiments, the anti-GPC3 antibody comprises a heavy chain comprising HVR-H1 sequence of SEQ ID NO:42, HVR-H2 sequence of SEQ ID NO:43, and HVR-H3 sequence of SEQ ID NO:44; and/or a light chain comprising HVR-L1 sequence of SEQ ID NO:45, HVR-L2 sequence of SEQ ID NO:46, and HVR-L3 sequence of SEQ ID NO:47. In some embodiments, the anti-GPC3 antibody comprises a heavy chain variable region comprising the amino acid sequence of SEQ ID NO:50 and/or a light chain variable region comprising the amino acid sequence of SEQ ID NO:51. In some embodiments, the anti-GPC3 antibody comprises a heavy chain comprising the amino acid sequence of SEQ ID NO:50 and/or a light chain comprising the amino acid sequence of SEQ ID NO:52. In some embodiments that can be combined with any other embodiments, the anti-GPC3 antibody is not GC33 or codrituzumab.

In some embodiments, the antibody described herein (e.g., a PD-1 axis binding antagonist antibody or an anti-GPC3 antibody) comprises an aglycosylation site mutation. In some embodiments, the aglycosylation site mutation is a substitution mutation. In some embodiments, the substitution mutation is at amino acid residue N297, L234, L235, and/or D265 (EU numbering). In some embodiments, the substitution mutation is selected from the group consisting of N297G, N297A, L234A, L235A, and D265A. In some embodiments, the substitution mutation is a D265A mutation and an N297G mutation. In some embodiments, the aglycosylation site mutation reduces effector function of the antibody. In some embodiments, the PD-1 axis binding antagonist (e.g., an anti-PD-1 antibody, an anti-PD-L1 antibody, or an anti-PD-L2 antibody) is a human IgG1 having Asn to Ala substitution at position 297 according to EU numbering.

In some embodiments of the methods, uses, compositions and kits described above and herein, the cancer is a GPC3-positive cancer. In some embodiments, the cancer is liver cancer, breast cancer, lung cancer, ovarian cancer, gastric cancer, bladder cancer, pancreatic cancer, endometrial cancer, colon cancer, kidney cancer, esophageal cancer, prostate cancer, or other cancers described herein. In some embodiments, the individual has cancer or has been diagnosed with cancer. In some embodiments, the cancer cells in the individual express PD-L1.

In some embodiments of the methods, uses, compositions, and kits described above and herein, the treatment or administration of the human PD-1 axis binding antagonist and the anti-GPC3 antibody results in a sustained response in the individual after cessation of the treatment. In some embodiments, the anti-GPC3 antibody is administered before the PD-1 axis binding antagonist, simultaneous with the PD-1 axis binding antagonist, or after the PD-1 axis binding antagonist. In some embodiments, the PD-1 axis binding antagonist and the anti-GPC3 antibody are in the same composition. In some embodiments, the PD-1 axis binding antagonist and the anti-GPC3 antibody are in separate compositions.

In some embodiments of the methods, uses, compositions, and kits described above and herein, the PD-1 axis binding antagonist and/or the anti-GPC3 antibody is administered intravenously, intramuscularly, subcutaneously, topically, orally, transdermally, intraperitoneally, intraorbitally, by implantation, by inhalation, intrathecally, intraventricularly, or intranasally. In some embodiments of the methods, uses, compositions, and kits described above and herein, the treatment further comprises administering a chemotherapeutic agent for treating or delaying progression of cancer in an individual. In some embodiments, the individual has been treated with a chemotherapeutic agent before the combination treatment with the PD-1 axis binding antagonist and the anti-GPC3 antibody. In some embodiments, the individual treated with the combination of the PD-1 axis binding antagonist and/or the anti-GPC3 antibody is refractory to a chemotherapeutic agent treatment. Some embodiments of the methods, uses, compositions, and kits described throughout the application, further comprise administering a chemotherapeutic agent for treating or delaying progression of cancer.

In some embodiments of the methods, uses, compositions and kits described above and herein, CD8 T cells in the individual have enhanced priming, activation, proliferation and/or cytolytic activity relative to prior to the administration of the combination. In some embodiments, the number of CD8 T cells is elevated relative to prior to administration of the combination. In some embodiments, the CD8 T cell is an antigen-specific CD8 T cell.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF DRAWINGS

FIG. 6C is a diagram showing the mean values of the body weight changes in the each treatment groups of mice bearing Hepa1-6 expressing human GPC3. SD bars are added.

DETAILED DESCRIPTION

Figure 1:
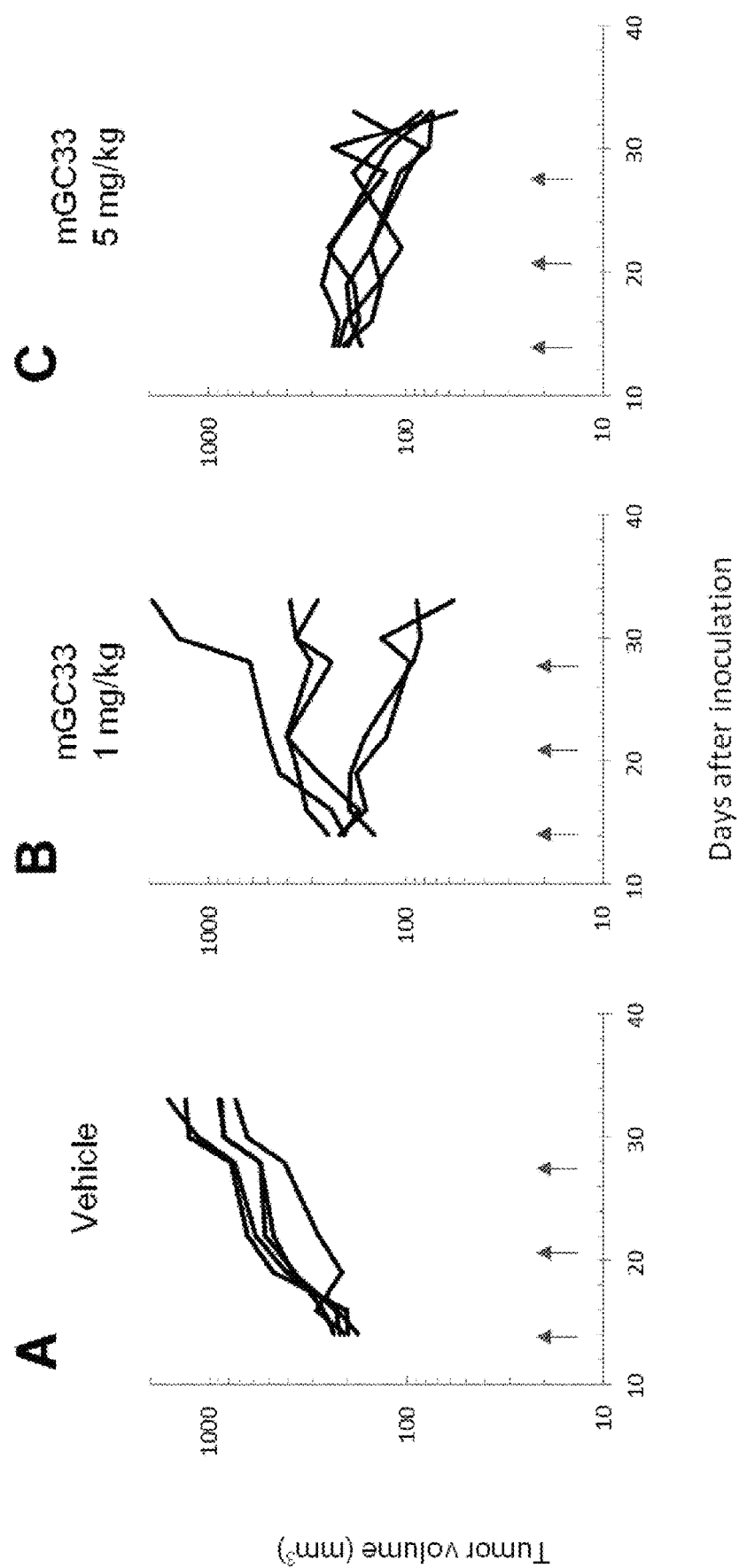
FIG. 1 is a diagram showing the Hepa1-6 expressing human GPC3 tumor volume changes in each mice treated three times weekly either by vehicle control, 1 mg/kg or 5 mg/kg of mGC33. Arrow indicates date of the injection. Five mice per each group were treated.

The data in the application show that the combination of an anti-GPC3 antibody with anti-PD-L1 immune therapy resulted in enhanced inhibition of tumor growth, increased response rates and durable responses. The inventors demonstrated the benefit of combining two therapies: the cytotoxic activity against GPC3 expressing tumor cells together with inhibiting the T cell suppressive PD-1/PD-L1 signaling results in enhanced therapeutic effects and durable long term responses.

In one aspect, provided herein are methods, compositions and uses for treating or delaying progression of cancer in an individual comprising administering an effective amount of a human PD-1 axis binding antagonist and an anti-GPC3 antibody.

In another aspect, provided herein are methods, compositions and uses for enhancing immune responses against tumor cells in an individual having cancer comprising administering an effective amount of a human PD-1 axis binding antagonist and an anti-GPC3 antibody. For example, enhanced immune responses against tumor cells includes infiltration of immune cells including macrophages and multinucleated giant cells in to tumor tissues. For another example, enhanced immune responses against tumor cells includes increase of CD45-positive lymphocytes, CD3ε-positive lymphocytes and CD8-positive T lymphocytes in tumor infiltrated lymphocytes (TILs).

I. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 or AMP-514 (MEDI0680) described herein. In another specific aspect, a PD-1 antagonist is selected from the group consisting of PDR001, REGN2810, BGB A317 and SHR-1210 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 or Atezolizumab described herein. In another specific aspect, an anti-PD-L1 antibody is MDX-1105 described herein. In another specific aspect, an anti-PD-L1 antibody is avelumab described herein. In still another specific aspect, an anti-PD-L1 antibody is MPDL3280A described herein. In still another specific aspect, an anti-PD-L1 antibody is MEDI4736 (durvalumab) described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of y-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenecity" refers to the ability of a particular substance to provoke an immune response. Tumors are immunogenic and enhancing tumor immunogenicity aids in the clearance of the tumor cells by the immune response. Examples of enhancing tumor immunogenicity include treatment with a PD-1 axis binding antagonistand an anti-GPC3 antibody.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0×length of the treatment duration.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, reducing tumor growth, decreasing symptoms resulting from the disease, increasing the quality of life of those suffering from the disease, decreasing the dose of other medications required to treat the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, gliblastoma, neuroblastomas, melanoma, breast carcinoma, gastric cancer, colorectal cancer (CRC), and hepatocellular carcinoma. Yet, in some embodiments, the cancer is selected from: non-small cell lung cancer, colorectal cancer, glioblastoma, breast carcinoma and hepatocellular carcinoma, including metastatic forms of those cancers.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from antimicrotubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signalling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine (e.g., erlotinib). In one embodiment the cytotoxic agent is a RAF inhibitor. In one embodiment, the RAF inhibitor is a BRAF and/or CRAF inhibitor. In one embodiment the RAF inhibitor is vemurafenib. In one embodiment the cytotoxic agent is a PI3K inhibitor.

"Chemotherapeutic agent" includes, but is not limited to, Nitrogen mustard analogues, Alkyl sulfonates, Ethylene imines, Nitrosoureas, Epoxides, other alkylating agents, Folic acid analogues, Purine analogues, Pyrimidine analogues, other antimetabolic agents, *Vinca* alkaloids or analogues, Podophyllotoxin derivatives, Camptothecan analogs, Colchicine derivatives, Taxanes, other plant alkaloids or natural products, Actinomycines, Anthracyclines or related substances, other cytotoxic antibiotics, Platinum compounds, Methylhydrazines, Kinase inhibitors, Enzymes, Histone Deacetylase Inhibitors, Retinoids, Immune checkpoint inhibitors, antibodies and other molecular target drug.

"Chemotherapeutic agent" also includes compounds useful in the treatment of cancer. Examples of chemotherapeutic agents include erlotinib (TARCEVA(registered), Genentech/OSI Pharm.), bortezomib (VELCADE(registered), Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX(registered), AstraZeneca), sunitib (SUTENT (registered), Pfizer/Sugen), letrozole (FEMARA(registered), Novartis), imatinib mesylate (GLEEVEC(registered), Novartis), finasunate (VATALANIB(registered), Novartis), oxaliplatin (ELOXATIN(registered), Sanofi), 5-FU (5-fluorouracil), leucovorin, Rapamycin (Sirolimus, RAPAMUNE(registered), Wyeth), Lapatinib (TYKERB (registered), GSK572016, Glaxo Smith Kline), Lonafamib (SCH 66336), sorafenib (NEXAVAR(registered), Bayer Labs), gefitinib (IRES SA(registered), AstraZeneca), AG1478, alkylating agents such as thiotepa and CYTOXAN (registered) cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1 I and calicheamicin ωII (Angew Chem. Intl. Ed. Engl. 1994 33: 183-186); dynemicin, including dynemicin A; bisphosphonates, such as clodronate; an esperamicin; as well as neocarzino statin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN(registered) (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK(registered) polysaccharide complex (JHS Natural Products, Eugene, Oreg.); razoxane; rhizoxin; sizofuran; spirogermanium; tenuazonic acid; triaziquone; 2,2', 2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE(registered) (Cremophor-free), albumin-engineered nanoparticle formulations of paclitaxel (American Pharmaceutical Partners, Schaumberg, Ill.), and TAXOTERE(registered) (docetaxel, doxetaxel; Sanofi-Aventis); chloranmbucil; GEMZAR(registered) (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE(registered) (vinorelbine); novantrone; teniposide; edatrexate; daunomycin; aminopterin; capecitabine (XELODA(registered)); ibandronate; CPT-11; topoisomerase inhibitor RFS 2000; difluoromethylomithine (DMFO); retinoids such as retinoic acid; and pharmaceutically acceptable salts, acids and derivatives of any of the above.

Chemotherapeutic agent also includes antibodies such as alemtuzumab (Campath), bevacizumab (AVASTIN(registered), Genentech); cetuximab (ERBITUX(registered), Imclone); panitumumab (VECTIBIX(registered), Amgen), rituximab (RITUXAN(registered), Genentech/Biogen Idec), pertuzumab (OMNITARG(registered), 2C4, Genentech), trastuzumab (HERCEPTIN(registered), Genentech), tositumomab (Bexxar, Corixia), and the antibody drug conjugate, gemtuzumab ozogamicin (MYLOTARG(registered), Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ, antibody genetically modified to recognize interleukin-12 p40 protein.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and anti-neoplastic drugs" by Murakami et al. (W. B. Saunders, Philadelphia, 1995), e.g., p. 13. The taxanes (paclitaxel and docetaxel) are anticancer drugs both derived from the yew tree. Docetaxel (TAXOTERE(registered), Rhone-Poulenc Rorer), derived from the European yew, is a semisynthetic analogue of paclitaxel (TAXOL (registered), Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("K") and lambda CO, based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2A, IgG2B, IgG3, IgG4, IgA1, and IgA2. The heavy chain constant domains that correspond to the different classes of immunoglobulins are called a, γ, ε, γ, and respectively. The subunit structures and three-dimensional configurations of different classes of immunoglobulins are well known and described generally in, for example, Abbas et al. Cellular and Mol. Immunology, 4th ed. (W. B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', F(ab')2, scFv and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthuen, in The Pharmacology of Monoclonal Antibodies, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9: 129-134 (2003); and Hollinger et al., Proc. Natl. Acad. Sci. USA 90: 6444-6448 (1993). Triabodies and tetrabodies are also described in Hudson et al., Nat. Med. 9: 129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature, 256:495-97 (1975); Hongo et al, Hybridoma, 14 (3): 253-260 (1995), Harlow et al., Antibodies: A Laboratory Manual, (Cold Spring Harbor Laboratory Press, 2nd ed. 1988); Hammerling et al, in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al, Nature, 352: 624-628 (1991); Marks et al, J. Mol. Biol. 222: 581-597 (1992); Sidhu et al, J. Mol. Biol. 338(2): 299-310 (2004); Lee et al, J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al, Year in Immunol. 7:33 (1993); U.S. Pat. Nos. 5,545,807; 5,545,806; 5,569,825; 5,625,126; 5,633,425; and U.S. Pat. No. 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al, Proc. Natl. Acad. Sci. USA 81:6851-6855 (1984)). Chimeric antibodies include PRIMATTZED(registered) antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al, Nature 321:522-525 (1986); Riechmann et al, Nature 332:323-329 (1988); and Presta, Curr. Op. Struct. Biol. 2:593-596 (1992). See also, e.g., Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE(trademark) technology). See also, for example, Li et al., Proc. Natl. Acad. Sci. USA, 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1 \times 10^{-7}$M, preferably no more than about $1 \times 10^{-8}$M and preferably no more than about $1 \times 10^{-9}$M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 Protein Eng, 8(10): 1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

II. PD-1 Axis Binding Antagonists

Provided herein is a method for treating or delaying progression of cancer in an individual comprising administering to the individual an effective amount of a PD-1 axis binding antagonist and an anti-GPC3 antibody. Also provided herein is a method of enhancing immune responses against tumor cells in an individual having cancer comprising administering to the individual an effective amount of a PD-1 axis binding antagonist and an anti-GPC3 antibody. For example, enhanced immune responses against tumor cells includes infiltration of immune cells including macrophages and multinucleated giant cells in to tumor tissues. For another example, enhanced immune responses against tumor cells includes increase of CD45-positive lymphocytes, CD3ε-positive lymphocytes and CD8-positive T lymphocytes in tumor infiltrated lymphocytes (TILs). For example, a PD-1 axis binding antagonist includes a PD-1 binding antagonist, a PD-L1 binding antagonist and a PD-L2 binding antagonist. PD-1 (programmed death 1) is also referred to in the art as "programmed cell death 1", PDCD1, CD279 and SLEB2. PD-L1 (programmed death ligand 1) is also referred to in the art as "programmed cell death 1 ligand 1", PDCD1LG1, CD274, B7-H, and PD-L1. PD-L2 (programmed death ligand 2) is also referred to in the art as "programmed cell death 1 ligand 2", PDCD1LG2, CD273, B7-DC, Btdc, and PDL2. In some embodiments, PD-1, PD-L1, and PD-L2 are human PD-1, PD-L1 and PD-L2.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106 (nivolumab), MK-3475 (lambrolizumab), and CT-011 (pidilizumab). In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224 or AMP-514 (MEDI0680). In some embodiments, the PD-1 binding antagonist is selected from the group consisting of PDR001, REGN2810, BGB A317 and SHR-1210. In some embodiments, the PD-L1 binding antagonist is anti-PD-L1 antibody. In some embodiments, the anti-PD-L1 binding antagonist is selected from the group consisting of YW243.55.S70, Atezolizumab, MPDL3280A, MDX-1105, avelumab, and MEDI4736 (durvalumab). Antibody YW243.55.S70 is an anti-PD-L1 described in WO2010/077634. MDX-1105, also known as BMS-936559, is an anti-PD-L1 antibody described in WO2007/005874. Avelumab is an anti-PDL1 antibody described in WO2013079174. MEDI4736 (durvalumab), is an anti-PD-L1 monoclonal antibody described in WO2011/066389 and US2013/034559. Nivolumab, also known as MDX-1106-04, MDX-1106, ONO-4538, BMS-936558, and OPDIVO(registered), is an anti-PD-1 antibody described in WO2006/121168. Pembrolizumab, also known as MK-3475, Merck 3475, lambrolizumab, KEYTRUDA (registered), and SCH-900475, is an anti-PD-1 antibody described in WO2009/114335. CT-011, also known as hBAT, hBAT-1 or pidilizumab, is an anti-PD-1 antibody described in WO2009/101611. AMP-224, also known as B7-DCIg, is a PD-L2-Fc fusion soluble receptor described in WO2010/027827 and WO2011/066342.

In some embodiments, the PD-1 axis binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fah)₂ fragments. In some embodiments, the anti-PD-L1 antibody is a humanized antibody. In some embodiments, the anti-PD-L1 antibody is a human antibody.

Examples of anti-PD-L1 antibodies useful for the methods of this invention, and methods for making thereof are described in PCT patent application WO2010/077634, WO2007/005874, WO2011/066389, and US2013/034559, which are incorporated herein by reference. The anti-PD-L1 antibodies useful in this invention, including compositions containing such antibodies, may be used in combination with an anti-GPC3 antibody to treat cancer.

Anti-PD1 Antibodies

In some embodiments, the anti-PD-1 antibody is MDX-1106. Alternative names for "MDX-1106" include MDX-1106-04, ONO-4538, BMS-936558 or Nivolumab. In some embodiments, the anti-PD-1 antibody is Nivolumab (CAS Registry Number: 946414-94-4). In a still further embodiment, provided is an isolated anti-PD-1 antibody comprising a heavy chain variable region comprising the heavy chain variable region amino acid sequence from SEQ ID NO:1 and/or a light chain variable region comprising the light chain variable region amino acid sequence from SEQ ID NO:2. In a still further embodiment, provided is an isolated anti-PD-1 antibody comprising a heavy chain and/or a light chain sequence, wherein:
(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence set forth in SEQ ID NO:1, and
(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence set forth in SEQ ID NO:2.

Anti-PD-L1 Antibodies

In some embodiments, the antibody in the formulation comprises at least one tryptophan (e.g., at least two, at least three, or at least four) in the heavy and/or light chain sequence. In some embodiments, amino acid tryptophan is in the CDR regions, framework regions and/or constant regions of the antibody. In some embodiments, the antibody comprises two or three tryptophan residues in the CDR regions. In some embodiments, the antibody in the formulation is an anti-PD-L1 antibody. PD-L1 (programmed death ligand 1), also known as PD-L1, B7-H1, B7-4, CD274, and B7-H, is a transmembrane protein, and its interaction with PD-1 inhibits T-cell activation and cytokine production. In some embodiments, the anti-PD-L1 antibody described herein binds to human PD-L1. Examples of anti-PD-L1 antibodies that can be used in the methods described herein are Atezolizumab, or anti-PD-L1 antibodies described in PCT patent application WO 2010/077634 A1 and U.S. Pat. No. 8,217,149, which are incorporated herein by reference.

In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody.

Anti-PD-L1 antibodies described in WO 2010/077634 A1 and U.S. Pat. No. 8,217,149 may be used in the methods described herein. In some embodiments, the anti-PD-L1 antibody comprises a heavy chain variable region sequence of SEQ ID NO:3 and/or a light chain variable region sequence of SEQ ID NO:4. In a still further embodiment, provided is an isolated anti-PD-L1 antibody comprising a heavy chain and/or a light chain sequence, wherein:
(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence set forth in SEQ ID NO:3, and
(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence set forth in SEQ ID NO:4.

In one embodiment, the anti-PD-L1 antibody comprises a heavy chain variable region polypeptide comprising an HVR-H1, HVR-H2 and HVR-H3 sequence, wherein:
(a) the HVR-H1 sequence is GFTFSX$_i$SWIH (SEQ ID NO:5);
(b) the HVR-H2 sequence is AWIX$_2$PYGGSX$_3$YYADSVKG (SEQ ID NO:6);
(c) the HVR-H3 sequence is RHWPGGFDY (SEQ ID NO:7);

further wherein: X$_1$ is D or G; X$_2$ is S or L; X$_3$ is T or S. In one specific aspect, X$_1$ is D; X$_2$ is S and X$_3$ is T.

In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

| | |
|---|---|
| HC-FR1 is EVQLVESGGGLVQPGGSLR LSCAAS | (SEQ ID NO:8) |
| HC-FR2 is WVRQAPGKGLEWV | (SEQ ID NO:9) |
| HC-FR3 is RFTISADTSKNTAYLQMNSLRAED-TAVYYCAR | (SEQ ID NO:10) |
| HC-FR4 is WGQGTLVTVSA | (SEQ ID NO:11). |

In a still further aspect, the heavy chain polypeptide is further combined with a variable region light chain comprising an HVR-L1, HVR-L2 and HVR-L3, wherein:

| | |
|---|---|
| (a) the HVR-L1 sequence is RASQX$_4$X$_5$ X$_6$TX$_7$X$_8$A | (SEQ ID NO:12); |
| (b) the HVR-L2 sequence is SASX$_9$LX$_{10}$S | (SEQ ID NO:13); |
| (c) the HVR-L3 sequence is QQX$_{11}$X$_{12}$X$_{13}$X$_{14}$PX$_{15}$T | (SEQ ID NO:14); | wherein: X$_4$ is D or V; X$_5$ is V or I; X$_6$ is S or N; X$_7$ is A or F; X$_8$ is V or L; X$_9$ is F or T; X$_{10}$ is Y or A; X$_{11}$ is Y, G, F, or S; X$_{12}$ is L, Y, F or W; X$_{13}$ is Y, N, A, T, G, F or I; X$_{14}$ is H, V, P, T or I; X$_{15}$ is A, W, R, P or T. In a still further aspect, X$_4$ is D; X$_5$ is V; X$_6$ is S; X$_7$ is A; X$_8$ is V; X$_9$ is F; X$_{10}$ is Y; X$_{11}$ is Y; X$_{12}$ is L; X$_{13}$ is Y; X$_{14}$ is H; X$_{15}$ is A.

In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

LC-FR1 is DIQMTQSPSSLSASVGDRVTITC (SEQ ID NO:15)

LC-FR2 is WYQQKPGKAPKLLIY (SEQ ID NO:16)

LC-FR3 is GVPSRFSGSGSGTDFTLTISSLQPED-FATYYC (SEQ ID NO:17)

LC-FR4 is FGQGTKVEIKR (SEQ ID NO:18).

In another embodiment, provided is an isolated anti-PD-L1 antibody or antigen binding fragment comprising a heavy chain and a light chain variable region sequence, wherein:
(a) the heavy chain comprises and HVR-H1, HVR-H2 and HVR-H3, wherein further:

(i) the HVR-H1 sequence is GFTFSX$_i$SWIH; (SEQ ID NO:5)

(ii) the HVR-H2 sequence is AWIX$_2$PYGGSX$_3$YYADSVKG (SEQ ID NO:6)

(iii) the HVR-H3 sequence is RHWPGGFDY, and (SEQ ID NO:7)

(b) the light chain comprises and HVR-L1, HVR-L2 and HVR-L3, wherein further:

(i) the HVR-L1 sequence is RASQX$_4$X$_5$X$_6$TX$_7$X$_8$ A (SEQ ID NO: 12)

(ii) the HVR-L2 sequence is SASX$_9$LX$_{10}$S; and (SEQ ID NO: 13)

(iii) the HVR-L3 sequence is QQX$_{11}$X$_{12}$X$_{13}$X$_{14}$PX$_{15}$T; (SEQ ID NO: 14)

wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a specific aspect, $X_1$ is D; $X_2$ is S and $X_3$ is T. In another aspect, $X_4$ is D; $X_5$ is V; $X_6$ is 5; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is 5; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, III or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2A, IgG2B, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region is IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:
(a) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, or
(b) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYH-PAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, III or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2A, IgG2B, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region is IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PD-L1 antibody comprising a heavy chain and a light chain variable region sequence, wherein:
(a) the heavy chain sequence has at least 85% sequence identity to the heavy chain sequence set forth in SEQ ID NO:25, and/or
(b) the light chain sequences has at least 85% sequence identity to the light chain sequence set forth in SEQ ID NO:4.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSS (SEQ ID NO:27).

In a still further aspect, the light chain framework sequences are derived from a Kabat kappa I, II, III or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2A, IgG2B, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region is IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

| | |
|---|---|
| HC-FR1 is EVQLVESGGGLVQPGGSLRLS-CAASGFTFS | (SEQ ID NO:29) |
| HC-FR2 is WVRQAPGKGLEWVA | (SEQ ID NO:30) |
| HC-FR3 is RFTISADTSKNTAYLQMNSLRAED-TAVYYCAR | (SEQ ID NO:10) |
| HC-FR4 is WGQGTLVTVSS | (SEQ ID NO:27). |

In a still further aspect, the light chain framework sequences are derived from a Kabat kappa I, II, III or IV subgroup sequence. In a still further aspect, the light chain framework sequences are VL kappa I consensus framework. In a still further aspect, one or more of the light chain framework sequences is the following:

| | |
|---|---|
| LC-FR1 is DIQMTQSPSSLSASVGDRVTITC | (SEQ ID NO: 15) |
| LC-FR2 is WYQQKPGKAPKLLIY | (SEQ ID NO: 16) |
| LC-FR3 is GVPSRFSGSGSGTDFTLTISSLQPED-FATYYC | (SEQ ID NO: 17) |
| LC-FR4 is FGQGTKVEIK | (SEQ ID NO: 28). |

In a still further specific aspect, the antibody further comprises a human or murine constant region. In a still further aspect, the human constant region is selected from the group consisting of IgG1, IgG2A, IgG2B, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region is IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:
(c) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, and/or
(d) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYHPAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSSASTK (SEQ ID NO:31).

In a still further aspect, the light chain framework sequences are derived from a Kabat kappa I, II, III or IV subgroup sequence. In a still further aspect, the light chain framework sequences are VL kappa I consensus framework. In a still further aspect, one or more of the light chain framework sequences are set forth as SEQ ID NOs:15, 16, 17 and 18. In a still further specific aspect, the antibody further comprises a human or murine constant region. In a still further aspect, the human constant region is selected from the group consisting of IgG1, IgG2A, IgG2B, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region is IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:
  (a) the heavy chain sequence has at least 85% sequence identity to the heavy chain sequence set forth in SEQ ID NO:26, or
  (b) the light chain sequences has at least 85% sequence identity to the light chain sequence set forth in SEQ ID NO:4.

In some embodiments, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO:4. In some embodiments, provided is an isolated anti-PD-L1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 26. In some embodiments, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:4 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:26. In some embodiments, one, two, three, four or five amino acid residues at the N-terminal of the heavy and/or light chain may be deleted, substituted or modified.

In a still further embodiment, provided is an isolated anti-PD-L1 antibody comprising a heavy chain and a light chain sequence, wherein:
  (a) the heavy chain sequence has at least 85% sequence identity to the heavy chain sequence set forth in SEQ ID NO:32, and/or
  (b) the light chain sequences has at least 85% sequence identity to the light chain sequence set forth in SEQ ID NO:33.

In a still further embodiment, provided is an isolated anti-PD-L1 antibody comprising a heavy chain and a light chain sequence, wherein:
  (a) the heavy chain sequence has at least 85% sequence identity to the heavy chain sequence set forth in SEQ ID NO: 55, and/or
  (b) the light chain sequences has at least 85% sequence identity to the light chain sequence set forth in SEQ ID NO:33.

In some embodiments, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33. In some embodiments, provided is an isolated anti-PD-L1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32 or 55. In some embodiments, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32 or 55.

In some embodiments, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the embodiments herein, the isolated anti-PD-L1 antibody can bind to a human PD-L1, for example a human PD-L1 as shown in UniProtKB/Swiss-Prot Accession No.Q9NZQ7.1, or a variant thereof.

In a still further embodiment, provided is an isolated nucleic acid encoding any of the antibodies described herein. In some embodiments, the nucleic acid further comprises a vector suitable for expression of the nucleic acid encoding any of the previously described anti-PD-L1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment.

III. Anti-GPC3 Antibodies

Provided herein is a method for treating or delaying progression of cancer in an individual comprising administering to the individual an effective amount of a PD-1 axis binding antagonist and an anti-GPC3 antibody. Also provided herein is a method of enhancing immune responses against tumor cells in an individual having cancer comprising administering to the individual an effective amount of a PD-1 axis binding antagonist and an anti-GPC3 antibody. For example, enhanced immune responses against tumor cells includes infiltration of immune cells including macrophages and multinucleated giant cells in to tumor tissues. For another example, enhanced immune responses against tumor cells includes increase of CD45-positive lymphocytes, CD3ε-positive lymphocytes and CD8-positive T lymphocytes in tumor infiltrated lymphocytes (TILs).

Provided herein are antibodies that bind to a human glypican 3 (GPC3). Alternative names for "GPC3" include SGB, DGSX, MXR7, SDYS, SGBS, OCI-5, SGBS1 and GTR2-2. The term "GPC3" as used herein, refers to any native GPC3 from any human source. The term encompasses "full-length" and unprocessed GPC3 as well as any form of GPC3 that results from processing in the cell (e.g., mature protein), including, but not limited to a C-terminal peptide of GPC3. The term also encompasses naturally occurring variants and isoforms of GPC3, e.g., splice variants or allelic variants. For example, descriptions of GPC3 and sequences are provided at UniProtKB/Swiss-Prot Accession No. P51654.1.

In some embodiments, the anti-GPC3 antibody binds to GPC3 and inhibits cell proliferation or growth of cancer cells. In some embodiments, the anti-GPC3 antibody is codrituzumab.

In some embodiments, an anti-GPC3 antibody can include an antibody-drug conjugate (ADC) (WO2007/137170) comprising a 1G12 antibody (WO2003/100429) (sold under catalog No. B0134R by BioMosaics Inc.) conjugated with a cytotoxic substance.

In some embodiments, an anti-GPC3 antibody is a humanized anti-GPC3 antibody described in WO2006/006693 or WO2007/047291.

In some embodiments, an anti-GPC3 antibody include a humanized anti-GPC3 antibody described in WO2006/006693 or WO2009/041062. In some embodiments, provided is a humanized anti-GPC3 antibody comprising a heavy chain and a light chain variable region sequence, wherein:

(a) the heavy chain comprises and HVR-H1, HVR-H2 and HVR-H3, wherein further:

(i) the HVR-H1 sequence is DYSMH     (SEQ ID NO:34)

(ii) the HVR-H2 sequence is WINTETGEPTY-ADDFKG     (SEQ ID NO:35)

(iii) the HVR-H3 sequence is LY     (SEQ ID NO:36)

(b) the light chain comprises and HVR-L1, HVR-L2 and HVR-L3, wherein further:

(i) the HVR-L1 sequence is KSSQSLLHSDGKT-FLN     (SEQ ID NO:37)

(ii) the HVR-L2 sequence is LVSRLDS     (SEQ ID NO:38)

(iii) the HVR-L3 sequence is CQGTHFPRT     (SEQ ID NO:39).

In a specific aspect, the anti-GPC3 antibody is humanized. The humanized anti-GPC3 antibody can be prepared using, as templates for humanization, appropriately selected human framework sequences having high sequence identity to a heavy chain framework sequence represented by SEQ ID NO:40 or a light chain framework sequence represented by SEQ ID NO:41.

In some embodiments, provided here is an anti-GPC3 chimeric antibody or a humanized anti-GPC3 antibody comprising a heavy chain and a light chain variable region sequence, wherein:

(a) the heavy chain comprises and HVR-H1, HVR-H2 and HVR-H3, wherein further:

(i) the HVR-H1 sequence is DYEMH     (SEQ ID NO:42)

(ii) the HVR-H2 sequence is ALDPKTGDTAY-SQKFKG     (SEQ ID NO:43)

(iii) the HVR-H3 sequence is FYSYTY     (SEQ ID NO:44)

(b) the light chain comprises and HVR-L1, HVR-L2 and HVR-L3, wherein further:

(i) the HVR-L1 sequence is RSSQSLVHSNRN-TYLH     (SEQ ID NO:45)

(ii) the HVR-L2 sequence is KVSNRFS     (SEQ ID NO:46)

(iii) the HVR-L3 sequence is SQNTHVPPT     (SEQ ID NO:47).

The humanized anti-GPC3 antibody can be prepared using, as templates for humanization, appropriately selected human framework sequences having high sequence identity to a heavy chain framework sequence represented by SEQ ID NO:48 or a light chain framework sequence represented by SEQ ID NO:49.

In a further embodiment, provided here is a humanized anti-GPC3 antibody capable of binding to an epitope to which a second antibody can bind, wherein said second antibody comprising a heavy chain and a light chain variable region sequence, wherein:

(a) the heavy chain comprises and HVR-H1, HVR-H2 and HVR-H3, wherein further:

(i) the HVR-H1 sequence is DYEMH     (SEQ ID NO:42)

(ii) the HVR-H2 sequence is ALDPKTGDTAY-SQKFKG     (SEQ ID NO:43)

(iii) the HVR-H3 sequence is FYSYTY     (SEQ ID NO:44)

(b) the light chain comprises and HVR-L1, HVR-L2 and HVR-L3, wherein further:

(i) the HVR-L1 sequence is RSSQSLVHSNRN-TYLH     (SEQ ID NO:45)

(ii) the HVR-L2 sequence is KVSNRFS     (SEQ ID NO:46)

(iii) the HVR-L3 sequence is SQNTHVPPT     (SEQ ID NO:47).

In a further embodiment, provided is a humanized anti-GPC3 antibody comprising a heavy chain variable region selected from the group of heavy chain variable regions represented by SEQ ID NOs:50 and a light chain variable region represented by SEQ ID NO:51. In a further alternative non-limiting aspect, provided is a humanized anti-GPC3 antibody comprising a heavy chain variable region selected from the group of heavy chain variable regions represented by SEQ ID NO:50 and a light chain variable region selected from the group of light chain variable regions represented by SEQ ID NO:52.

In a still further embodiment, provided is a humanized anti-GPC3 antibody comprising a heavy chain variable region represented by SEQ ID NO:53 and a light chain variable region represented by SEQ ID NO:54.

Alternative examples of the anti-GPC3 antibody of the present invention include an anti-GPC3 antibody having cytotoxic activity. In the present invention, non-limiting examples of the cytotoxic activity include antibody-dependent cell-mediated cytotoxicity or antibody-dependent cellular cytotoxicity (ADCC) activity, complement-dependent cytotoxicity (CDC) activity, and cytotoxic activity based on T cells. In the present invention, the CDC activity means cytotoxic activity brought about by the complement system. On the other hand, the ADCC activity means the activity of damaging target cells by, for example, immunocytes, through the binding of the immunocytes via Fcγ receptors expressed on the immunocytes to the Fc regions of antigen-binding molecules comprising antigen-binding domains capable of binding to membrane molecules expressed on the cell membranes of the target cells. Whether or not the antigen-binding molecule of interest has ADCC activity or has CDC activity can be determined by a method known in the art (e.g., Current protocols in Immunology, Chapter 7. Immunologic studies in humans, Coligan et al., ed. (1993)).

In some embodiments, alternative examples of the anti-GPC3 antibody of the present invention include an anti-GPC3 antibody conjugated with a cytotoxic substance. Such an anti-GPC3 antibody-drug conjugate (ADC) is specifically disclosed in, for example, WO2007/137170, though the conjugate of the present invention is not limited to those described therein. Specifically, the cytotoxic substance may be any of chemotherapeutic agents listed below or may be a compound disclosed in Alley et al. (Curr. Opin. Chem. Biol. (2010) 14, 529-537) or WO2009/140242. Antigen-binding molecules are conjugated with these compounds via appropriate linkers or the like.

In some embodiments, alternative examples of the anti-GPC3 antibody of the present invention include an anti-GPC3 antibody comprises an FcγR-binding modified Fc region having higher binding activity against Fcγ receptors than that of the Fc region of native human IgG against Fcγ receptors. The modification can include amino acid modification at any position as long as the resulting Fc region has higher binding activity against Fcγ receptors than that of the native human IgG Fc region against Fcγ receptors. When the antigen-binding molecule contains a human IgG1 Fc region as a human Fc region, the modification preferably allows the Fc region to contain a fucose-containing sugar chain as a sugar chain bound to position 297 (EU numbering) and is effective for producing higher binding activity against Fcγ receptors than that of the native human IgG Fc region against Fcγ receptors. Such amino acid modification has been reported in, for example, International Publication Nos. WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, WO2006/023403, and WO2014/097648.

In some embodiments, the Fc region contained in the anti-GPC3 antibody provided by the present invention can also include an Fc region modified such that a higher proportion of fucose-deficient sugar chains is bound to the Fc region or a higher proportion of bisecting N-acetylglucosamine is added to the Fc region in the composition of sugar chains bound to the Fc region. WO2006/046751 and WO2009/041062 disclose specific examples of the anti-GPC3 antibody comprising the Fc region modified such that a higher proportion of fucose-deficient sugar chains is bound to the Fc region or a higher proportion of bisecting N-acetylglucosamine is added to the Fc region in the composition of sugar chains bound to the Fc region.

In some embodiments, the anti-GPC3 antibody that may be used in the present invention include an anti-GPC3 antibody having an amino acid residue modified to alter its isoelectric point (pI). Preferred examples of the "alteration of the electric charge of an amino acid residue" in the anti-GPC3 antibody are described in WO2009/041062.

In some embodiments, the anti-GPC3 antibody includes a modified form of the antibody that has received a posttranslational modification of the polypeptide constituting the primary structure of the anti-GPC3 antibody. The posttranslational modification of a polypeptide refers to chemical modification given to the polypeptide translated during polypeptide biosynthesis. For example, an anti-GPC3 antibody that has received the modification of N-terminal glutamine to pyroglutamic acid by pyroglutamylation is also included in the anti-GPC3 antibody of the present invention, as a matter of course. Also, for example, a posttranslationally modified anti-GPC3 antibody comprising heavy and light chains or heavy chains linked via a "disulfide bond", which means a covalent bond formed between two sulfur atoms is included in the anti-GPC3 antibody of the present invention. A thiol group contained in an amino acid cysteine can form a disulfide bond or crosslink with a second thiol group. In general IgG molecules, CH1 and CL regions are linked via a disulfide bond, and two polypeptides constituting heavy chains are linked via a disulfide bond between cysteine residues at positions 226 and 229 based on the EU numbering. A posttranslationally modified anti-GPC3 antibody having such a linkage via a disulfide bond is also included in the anti-GPC3 antibody of the present invention.

In a still further embodiment, provided is an isolated nucleic acid encoding any of the antibodies described herein. In some embodiments, the nucleic acid further comprises a vector suitable for expression of the nucleic acid encoding any of the previously described anti-GPC3 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-GPC3 antibodies or antigen-binding fragment in a form suitable for expression, under conditions suitable to produce such antibody or fragment, and recovering the antibody or fragment.

IV. Antibody Preparation

The antibody described herein is prepared using techniques available in the art for generating antibodies, exemplary methods of which are described in more detail in the following sections.

The antibody is directed against an antigen of interest (i.e., PD-L1 (such as a human PD-L1) or GPC3 (such as a human glypican 3)). Preferably, the antigen is a biologically important polypeptide and administration of the antibody to a mammal suffering from a disorder can result in a therapeutic benefit in that mammal.

In certain embodiments, an antibody provided herein has a dissociation constant (Kd) of ≤1μ,M, ≤150 nM, ≤100 nM, ≤50 nM, ≤10 nM, ≤1 nM, ≤0.1 nM, ≤0.01 nM, or ≤0.001 nM (e.g., 10-8M or less, e.g., from 10-8M to 10-13M, e.g., from 10-9M to 10-13M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125D-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER(registered) multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$]1-antigen are mixed with serial dilutions of a Fab of interest. The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20(registered)) in PBS. When the plates have dried, 150 μl/well of scintillant (MICROSCINT-20(trade mark); Packard) is added, and the plates are counted on a TOPCOUNT(trade mark) gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE(registered)-2000 or a BIACORE(registered)-3000 (BIAcore, Inc., Piscataway, N.J.) at 25° C. with immobilized antigen CMS chips at ~10 response units (RU). Briefly, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (—0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20(trade mark)) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE (registered) Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO(trade mark) spectrophotometer (ThermoSpectronic) with a stirred cuvette.

(i) Antigen Preparation

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹/₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the invention can be made using the hybridoma method first described by Kohler et al., Nature, 256:495 (1975), and further described, e.g., in Hongo et al., Hybridoma, 14(3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), and Ni, Xiandai Mianyixue, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, Histology and Histopathology, 20(3):927-937 (2005) and Vollmers and Brandlein, Methods and Findings in Experimental and Clinical Pharmacology, 27(3): 185-91 (2005).

For various other hybridoma techniques, see, e.g., US2006/258841; US2006/183887 (fully human antibodies), US2006/059575; US2005/287149; US2005/100546; US2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of the invention or a fragment thereof, and an adjuvant, such as monophosphoryl lipid A (MPL)/trehalose dicrynomycolate (TDM) (Ribi Immunochem. Research, Inc., Hamilton, Mont.). A polypeptide of the invention (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, Monoclonal Antibodies: Principles and Practice, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al, Monoclonal Antibody Production Techniques and Applications, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., Trends in Biotechnology, 24(3), 105-108 (2006).

Oligopeptides as tools for improving productivity of hybridoma cell cultures are described in Franek, Trends in Monoclonal Antibody Research, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the invention. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al, Anal. Biochem., 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US2005/176122 and U.S. Pat. No. 6,919,436. The method includes using minimal salts, such as lyotropic salts, in the binding process and preferably also using small amounts of organic solvents in the elution process.

(iii) Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Additional methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352:624-628 (1991); Marks et al., J. Mol. Biol. 222:581-597 (1992); Marks and Bradbury, in Methods in Molecular Biology 248:161-175 (Lo, ed., Human Press, Totowa, N.J., 2003); Sidhu et al., J. Mol. Biol. 338(2):299-310 (2004); Lee et al., J. Mol. Biol. 340(5):1073-1093 (2004); Fellouse, Proc. Natl. Acad. Sci. USA 101(34):12467-12472 (2004); and Lee et al., J. Immunol. Methods 284(1-2):119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol, 12:433-455 (1994). Phage typically display antibody fragments, either as single-chain FAT (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self-antigens without any immunization as described by Griffiths et al., EMBO J, 12:725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

(iv) Chimeric, Humanized and Human Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'lAcad. Sci. USA 86:10029-10033 (1989); U.S. Pat. Nos. 5/821,337, 7/527,791, 6/982,321, and 7/087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol, 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In certain embodiments, an antibody provided herein is a human antibody. Human antibodies can be produced using various techniques known in the art. Human antibodies are described generally in van Dijk and van de Winkel, Curr. Opin. Pharmacol. 5:368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE(trade mark) technology; U.S. Pat. No. 5,770,429 describing HUMAB(registered) technology; U.S. Pat. No. 7,041,870 describing K-M MOUSE(registered) technology, and U.S. Patent Application Publication No. US2007/0061900, describing VELOCIMOUSE(registered) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol, 133:3001 (1984); Brodeur et al., Monoclonal Antibody Production Techniques and Applications, pp. 51-63 (Marcel Dekker, Inc., New York, 1987); and Boerner et al., J. Immunol., 147:86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167

(1992)). According to another approach, F(ab') 2 fragments can be isolated directly from recombinant host cell culture. Fab and F(ab') 2 fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

(vi) Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516). In one embodiment, a single-domain antibody consists of all or a portion of the heavy chain variable domain of an antibody.

(vii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(viii) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "Preferred Substitutions." More substantial changes are provided in Table 1 under the heading of "Exemplary Substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

Exemplary Substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |

TABLE 1-continued

Exemplary Substitutions.

| Original Residue | Exemplary Substitutions | Preferred Substitutions |
|---|---|---|
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln: Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp: Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

a. hydrophobic: Norleucine, Met, Ala, Val, Leu, Ile;
b. neutral hydrophilic: Cys, Ser, Thr, Asn, Gln;
c. acidic: Asp, Glu;
d. basic: His, Lys, Arg;
e. residues that influence chain orientation: Gly, Pro;
f. aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

(ix) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided comprising an Fc region wherein a carbohydrate structure attached to the Fc region has reduced fucose or lacks fucose, which may improve ADCC function. Specifically, antibodies are contemplated herein that have reduced fusose relative to the amount of fucose on the same antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In certain embodiments, the antibody is one wherein less than about 50%, 40%, 30%, 20%, 10%, or 5% of the N-linked glycans thereon comprise fucose. For example, the amount of fucose in such an antibody may be from 1% to 80%, from 1% to 65%, from 5% to 65% or from 20% to 40%. In certain embodiments, the antibody is one wherein none of the N-linked glycans thereon comprise fucose, i.e., wherein the antibody is completely without fucose, or has no fucose or is afucosylated. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US2003/0157108 (Presta, L.); US2004/0093621 (Kyowa Hakko Kogyo Co., Ltd). Examples of publications related to "defucosylated" or "fucose-deficient" antibody variants include: US2003/0157108; WO2000/61739; WO2001/29246; US2003/0115614; US2002/0164328; US2004/0093621; US2004/0132140; US2004/0110704; US2004/0110282; US2004/0109865; WO2003/085119; WO2003/084570; WO2005/035586; WO2005/035778; WO2005/053742; WO2002/031140; Okazaki et al. J. Mol. Biol. 336:1239-1249 (2004); Yamane-Ohnuki et al. Biotech. Bioeng. 87:614 (2004). Examples of cell lines capable of producing defucosylated antibodies include Lec13 CHO cells deficient in protein fucosylation (Ripka et al. Arch. Biochem. Biophys. 249: 533-545 (1986); US Patent Publication No. US2003/0157108, Presta, L; and WO2004/056312, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87:614 (2004); Kanda, Y. et al., Biotechnol. Bioeng., 94(4): 680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO2003/011878 (Jean-Mairet et al.); U.S. Pat. No. 6,602,684 (Umana et al.); US2005/0123546 (Umana et al.), and Ferrara et al., Biotechnology and Bioengineering, 93(5):851-861 (2006). Antibody variants with at least one galactose residue in the oligosaccharide attached to the Fc region are also provided. Such antibody variants may have improved CDC function. Such antibody variants are described, e.g., in WO1997/30087 (Patel et al.); WO1998/58964 (Raju, S.); and WO1999/22764 (Raju, S.).

In certain embodiments, the antibody variants comprising an Fc region described herein are capable of binding to an FcγRIII. In certain embodiments, the antibody variants comprising an Fc region described herein have ADCC activity in the presence of human effector cells or have increased ADCC activity in the presence of human effector cells compared to the otherwise same antibody comprising a human wild-type IgG1 Fc region.

(x) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'lAcad. Sci. USA 83:7059-7063 (1986)) and Hellstrom, I. et al., Proc. Nat'lAcad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI(trade mark) non-radioactive cytotoxicity assay for flow cytometry (CellTechnology, Inc. Mountain View, Calif.; and CytoTox 96(registered) non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'lAcad. Sci. USA 95:652-656 (1998). Clq binding assays may also be carried out to confirm that the antibody is unable to bind Clq and hence lacks CDC activity. See, e.g., Clq and C3c binding ELISA in WO2006/029879 and WO2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO2004/056312, and Shields et al., J. Biol. Chem. 9(2):6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues). In an exemplary embodiment, the antibody comprising the following amino acid substitutions in its Fc region: S298A, E333A, and K334A.

In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO99/51642, and Idusogie et al. J. Immunol. 164:4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.)). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO94/29351 concerning other examples of Fc region variants.

(xi) Antibody Derivatives

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(xii) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ. plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp 1 gene present in the yeast plasmid YRp7 (Stinchcomb et al., Nature, 282:39 (1979)). The trp 1 gene provides a selection marker for a mutant strain of yeast lacking the ability to grow in tryptophan, for example, ATCC No. 44076 or PEP4-1. Jones, Genetics, 85:12 (1977). The presence of the trp 1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, 0-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human (3-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* $X_{1776}$ (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP402,226); *Pichia pastoris* (EP183,070); *Candida*; *Trichoderma reesia* (EP244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, Nat. Biotech. 22:1409-1414 (2004).

Certain fungi and yeast strains may be selected in which glycosylation pathways have been "humanized," resulting in the production of an antibody with a partially or fully human glycosylation pattern. See, e.g., Li et al., Nat. Biotech. 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells.

Plant cell cultures of cotton, corn, potato, soybean, *petunia*, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES(trade mark) technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al, J. Gen Virol. 36:59 (1977)); baby hamster kidney cells (BHK, ATCC CCL 10); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al, Annals NY. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR- CHO cells (Urlaub et al, Proc. Natl. Acad. Sci. USA 77:4216 (1980)); and myeloma cell lines such as NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO90/03430; WO87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN(trade mark) drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xiii) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX(trade mark) resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE(trade mark) chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

C. Selecting Biologically Active Antibodies

Antibodies produced as described above may be subjected to one or more "biological activity" assays to select an antibody with beneficial properties from a therapeutic perspective or selecting formulations and conditions that retain biological activity of the antibody. The antibody may be tested for its ability to bind the antigen against which it was raised. For example, methods known in the art (such as ELISA, Western Blot, etc.) may be used.

For example, for an anti-PD-L1 antibody, the antigen binding properties of the antibody can be evaluated in an assay that detects the ability to bind to PD-L1. In some embodiments, the binding of the antibody may be determined by saturation binding; ELISA; and/or competition assays (e.g. RIA's), for example. Also, the antibody may be subjected to other biological activity assays, e.g., in order to evaluate its effectiveness as a therapeutic. Such assays are known in the art and depend on the target antigen and intended use for the antibody. For example, the biological effects of PD-L1 blockade by the antibody can be assessed in CD8+ T cells, a lymphocytic choriomeningitis virus (LCMV) mouse model and/or a syngeneic tumor model e.g., as described in U.S. Pat. No. 8,217,149.

To screen for antibodies which bind to a particular epitope on the antigen of interest (e.g., those which block binding of the anti-PD-L1 antibody of the example to PD-L1), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al., J. Biol. Chem. 270:1388-1394 (1995), can be performed to determine whether the antibody binds an epitope of interest.

D. Pharmaceutical Compositions and Formulations

Also provided herein are pharmaceutical compositions and formulations comprising a PD-1 axis binding antagonist and/or an antibody described herein (such as an anti-PD-L1 antibody or an anti-GPC3 antibody) as an active ingredient and a pharmaceutically acceptable carrier.

"Combination" as described herein refers to a combination of active ingredients for combination use, and includes both modes where separate substances are used in combination upon administration or where they are provided as a mixture (combination preparation).

Pharmaceutical compositions and formulations as described herein can be prepared by mixing active ingredients (such as an anti-PD-L1 antibody and/or an anti-GPC3 antibody) having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX(registered), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer. In some embodiments, the anti-PD-L1 antibody described herein is in a formulation comprising the antibody in a concentration of about 60 mg/mL, histidine acetate in a concentration of about 20 mM, sucrose in a concentration of about 120 mM, and polysorbate (e.g., polysorbate 20) in a concentration of 0.04% (w/v), and the formulation has a pH of about 5.8. In some embodiments, the anti-PD-L1 antibody described herein is in a formulation comprising the antibody in a concentration of about 125 mg/mL, histidine acetate in a concentration of about 20 mM, sucrose is in a concentration of about 240 mM, and polysorbate (e.g., polysorbate 20) in a concentration of 0.02% (w/v), and the formulation has a pH of about 5.5.

The composition and formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. The formulations to be used for in vivo administration are generally sterile. Sterility may be readily accomplished, e.g., by filtration through sterile filtration membranes.

IV. Methods of Treatment

Provided herein are methods for treating, preventing or delaying progression of cancer in an individual comprising administering to the individual an effective amount of a PD-1 axis binding antagonist and an anti-GPC3 antibody. In some embodiments, the treatment results in a sustained response in the individual after cessation of the treatment. The methods described herein may find use in treating conditions where enhanced immunogenicity is desired such as increasing tumor immunogenicity for the treatment of cancer. Also provided herein are methods of enhancing immune responses against tumor cells in an individual having cancer comprising administering to the individual an effective amount of a PD-1 axis binding antagonist and an anti-GPC3 antibody. For example, enhanced immune responses against tumor cells includes infiltration of immune cells including macrophages and multinucleated giant cells in to tumor tissues. For another example, enhanced immune responses against tumor cells includes increase of CD45- positive lymphocytes, CD3ε-positive lymphocytes and CD8-positive T lymphocytes in tumor infiltrated lymphocytes (TILs). Any of the PD-1 axis binding antagonists and the anti-GPC3 antibodies known in the art or described herein may be used in the methods.

In some embodiments, the individual is a human. In some embodiments, the individual has GPC3 positive cancer. In some embodiments, GPC3 positive cancer is liver cancer, breast cancer, lung cancer, ovarian cancer, gastric cancer, bladder cancer, pancreatic cancer, endometrial cancer, colon cancer, kidney cancer, esophageal cancer, or prostate cancer. In some embodiments the liver cancer is a hepatocellular carcinoma. In some embodiments, the breast cancer is a breast carcinoma or a breast adenocarcinoma. In some embodiments, the breast carcinoma is an invasive ductal carcinoma. In some embodiments, the lung cancer is a lung adenocarcinoma. In some embodiments, the colon cancer is a colorectal adenocarcinoma. In some embodiments, the cancer cells in the individual express PD-L1. In some embodiments, the cancer cells in the individual express GPC3 protein at a level that is detectable (e.g., detectable using methods known in the art).

In some embodiments, the individual has been treated with a GPC3 targeted therapy before the combination treatment with a PD-1 axis binding antagonist and an anti-GPC3 antibody. In some embodiments, the GPC3 targeted therapy includes treatment with one or more small molecules, e.g., sorafenib.

In some embodiments, the combination therapy of the invention comprises administration of a PD-1 axis binding antagonist and an anti-GPC3 antibody. The PD-1 axis binding antagonist and the anti-GPC3 antibody may be administered in any suitable manner known in the art. For example, The PD-1 axis binding antagonist and the anti-GPC3 antibody may be administered sequentially (at different times) or concurrently (at the same time). In some embodiments, the PD-1 axis binding antagonist is in a separate composition as the anti-GPC3 antibody. In some embodiments, the PD-1 axis binding antagonist is in the same composition as the anti-GPC3 antibody.

The PD-1 axis binding antagonist and the anti-GPC3 antibody may be administered by the same route of administration or by different routes of administration. In some embodiments, the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally. In some embodiments, the anti-GPC3 antibody is administered intravenously, intramuscularly, subcutaneously, topically, orally, transdermally, intraperitoneally, intraorbitally, by implantation, by inhalation, intrathecally, intraventricularly, or intranasally. An effective amount of the PD-1 axis binding antagonist and the anti-GPC3 antibody may be administered for prevention or treatment of disease. The appropriate dosage of the PD-1 axis binding antagonist and/or the anti-GPC3 antibody may be determined based on the type of disease to be treated, the type of the PD-1 axis binding antagonist and the anti-GPC3 antibody, the severity and course of the disease, the clinical condition of the individual, the individual's clinical history and response to the treatment, and the discretion of the attending physician.

As a general proposition, the therapeutically effective amount of the antibody administered to human will be in the range of about 0.01 to about 50 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antibody is administered at 15 mg/kg. However, other dosage regimens may be useful. In one embodiment, an anti-PD-L1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some embodiments, the methods may further comprise an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PI3K/AKT/mTOR pathway, HSP90 inhibitor, tubulin inhibitor, apoptosis inhibitor, and/or chemopreventative agent. The additional therapy may be one or more of the chemotherapeutic agents described herein.

V. Articles of Manufacture or Kits

In another embodiment of the invention, an article of manufacture or a kit is provided comprising a PD-1 axis binding antagonist and/or an anti-GPC3 antibody. In some embodiments, the article of manufacture or kit further comprises package insert comprising instructions for suing the PD-1 axis binding antagonist in conjunction with an anti-GPC3 antibody to treat or delay progression of cancer in an individual or to enhance immune responses against tumor cells of an individual having cancer. For example, enhanced immune responses against tumor cells includes infiltration of immune cells including macrophages and multinucleated giant cells in to tumor tissues. For another example, enhanced immune responses against tumor cells includes increase of CD45-positive lymphocytes, CD3ε-positive lymphocytes and CD8-positive T lymphocytes in tumor infiltrated lymphocytes (TILs). Any of the PD-1 axis binding antagonist and/or anti-GPC3 antibodies described herein may be included in the article of manufacture or kits.

In some embodiments, the PD-1 axis binding antagonist and the anti-GPC3 antibody are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

Example 1

Mouse Cell Lines Expressing Human Glypican-3 (GPC3)

Mouse cancer cell lines, Hepa1-6 (ATCC No. CRL-1830) and CT26 (ATCC No. CRL-2638) were transfected with human GPC3 expression vector, pCXND2/hGPC3(FL) [Ishiguro T. et al., Cancer Res. 2008; 68: 9832-9838] using FuGENE6 (Roche Diagnostics Corp) and selected with 1 mg/mL G418 (Invitrogen). Cells that grew even in the presence of G418 were collected, and the colonies were isolated by limiting dilution. Expression of human GPC3 were confirmed by FACS using anti-human GPC3 antibody, GC33 [Ishiguro T. et al., Cancer Res. 2008; 68: 9832-9838]. Representative clones were selected and used for the experiments.

Example 2

Anti-tumor activity of anti-GPC3 antibody in syngenic mouse model using Hepa1-6 cell line expressing human GPC3

Hepa1-6/hGPC3 cells were cultured using cell culture flasks in an incubator (set at 37° C. and 5% $CO_2$). The cells were detached from the flasks with trypsin and washed with D MEM containing 10% (v/v) FBS, 0.6 mg/mL G418. Then the cells were re-suspended in D-MEM ($2\times10^8$ cells/mL), and an equal volume of Matrigel was added. The cell concentrations for implantation were $1\times10^8$ cells/mL. The cells were inoculated subcutaneously into the right flank of each C57BL/6J mouse (Charles River Laboratories Japan) ($1\times10^7$ cells/mouse). Once palpable tumors were established, animals were randomized into testing groups so that each group had similar mean tumor volumes when the study started. Either 1 or 5 mg/kg of mouse GC33 anti-human GPC3 monoclonal antibody [WO2006/006693] diluted in PBS, or PBS as a vehicle control was injected at day 14, 21 and 28 intravenously after tumor inoculation. Mouse GC33 showed inhibition of tumor growth with dose dependency compared to vehicle control (FIG. 1).

Example 3

Pathological Changes Induced by Anti-GPC3 Antibody in Syngenic Mouse Model Using Hepa1-6 Cell Line Expressing Human GPC3

To assess the changes in the Hepa1-6 tumor tissue by mouse GC33 treatment, tumor tissue isolated either after 3 or 7 days from the single injection either of mouse GC33 antibody or vehicle control was used for the pathological examination. Tumor tissues were fixed by 4% parafolmaldehyde (PFA) and embedded in paraffin by the AMeX method [Suzuki et al, J Toxicol Sci. 2002; 27:165-172, Watanabe et al, J Toxicol Pathol. 2015; 28: 43-49]. Three micro-meter paraffin sections were stained with hematoxylin and eosin (HE) or immunohistochemically (IHC). IHC staining was performed according to the labeled streptavidin-biotin (LSAB) method (RTU horseradish peroxidase streptavidin). Antibodies against F4/80 (marker antigen of murine macrophages; A3-1, BioLegend), PD-L1 (marker antigen of mouse B7-H1/PD-L1; AF1019, R&D systems) were used as the primary antibodies. The positive signals were visualized by the peroxidase-diaminobenzidine reaction, and the sections were counterstained with hematoxylin.

Figure 2A:
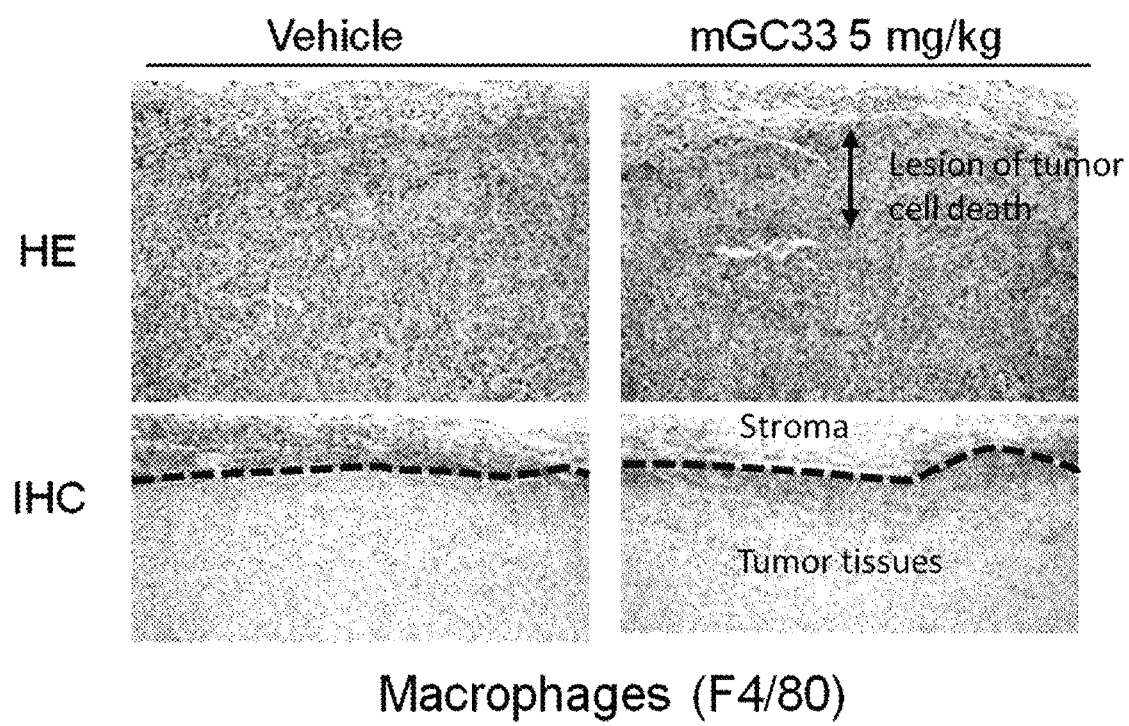
FIG. 2A is a diagram showing the images of hematoxylin and eosin staining (HE) or F4/80 immune-histochemical staining (IHC) of tissues isolated from the mice treated either by vehicle control or 5 mg/kg of mGC33.
Figure 2B:
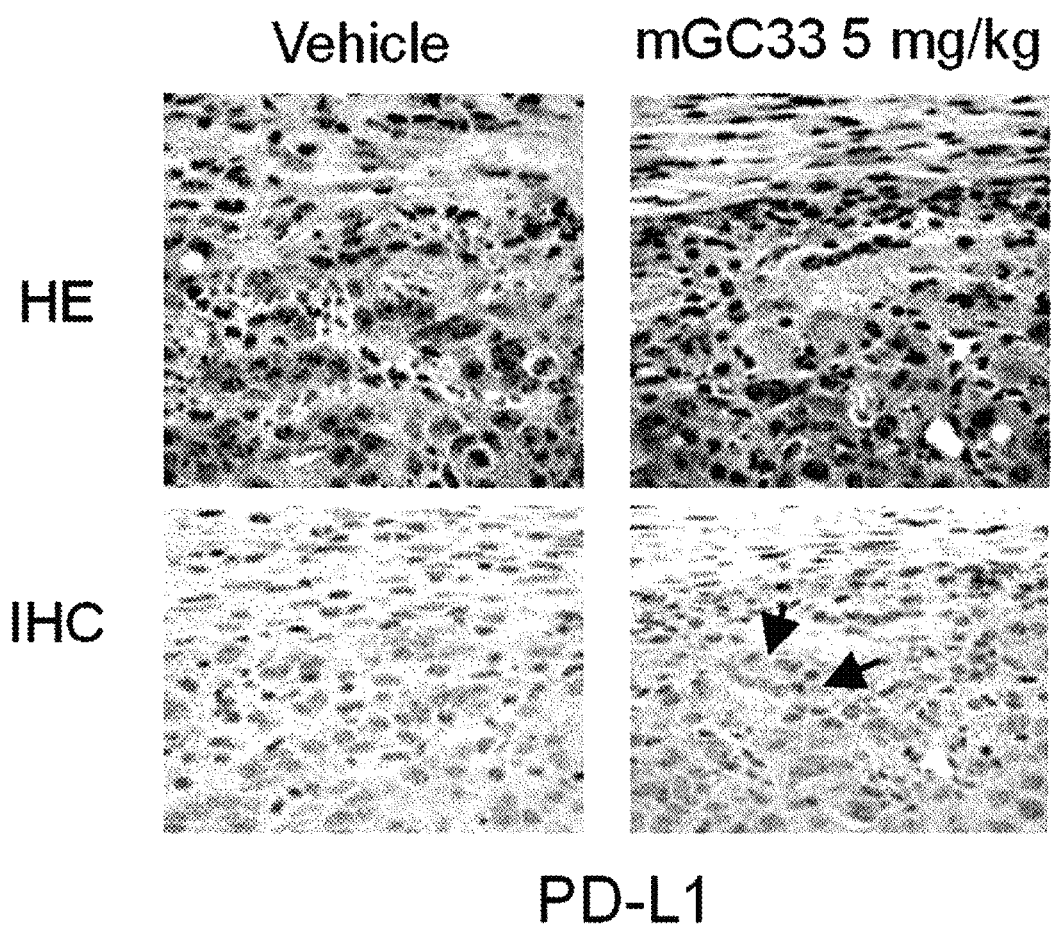
FIG. 2B is a diagram showing the images of hematoxylin and eosin staining (HE) or PD-L1 immune-histochemical staining (IHC) of tissues isolated from the mice treated either by vehicle control or 5 mg/kg of mGC33. Arrow indicates PD-L1 immunoreactivity observed in cell membranes of infiltrated immune cells.

By mouse GC33 injection, immune cell infiltrations and tumor cell death were observed in the peripheral regions of the tumor tissues. Also increased infiltration of F4/80 positive macrophage cells were observed in the area in which tumor cell death was observed in the tumor tissues treated by mouse GC33, while F4/80 positive cells mainly observed in the stromal regions in the tumor tissue with vehicle control (FIG. 2A). Subsequently, PD-L1 expression was increased by mouse GC33 especially on the infiltrated immune cells, compared to vehicle control, which suggested that PD-L1 might be induced to suppress the anti-tumor activity by mouse GC33 (FIG. 2B).

Example 4

Anti-Tumor Activity in Combination with the Anti-GPC3 (GC33) and Anti-PD-L1 Antibodies (10F.9G2) in Syngenic Mouse Model Using CT26 Cell Line Expressing Human GPC3

To evaluate anti-tumor activities of anti-GPC3 or anti-PD-L1 monotherapies or combination in mouse CT26/hGPC3 model, either mouse GC33 antibody and/or 500 µg of anti-mouse PD-L1 rat antibody, 10F.9G2 (purchased from BioXCell) were injected either from day 3 (early treatment model) or day 15 (established model) after subcutaneously inoculation of $1\times10^6$ of CT26/hGPC3 cells. In the early treatment model, either 5 or 25 mg/kg of mouse GC33 was injected at day 3, 6, 10 and 13 intravenously, and 500 µg of anti-PD-L1 antibody, 10F.9G2, was injected at same schedule as single agent or combination. In establishment model, either 5 or 25 mg/kg of mouse GC33 was injected at day 15 and 18 intravenously, and 500 µg of anti-PD-L1 antibody, 10F.9G2, was injected at same schedule as single agent or combination.

Figure 3A:
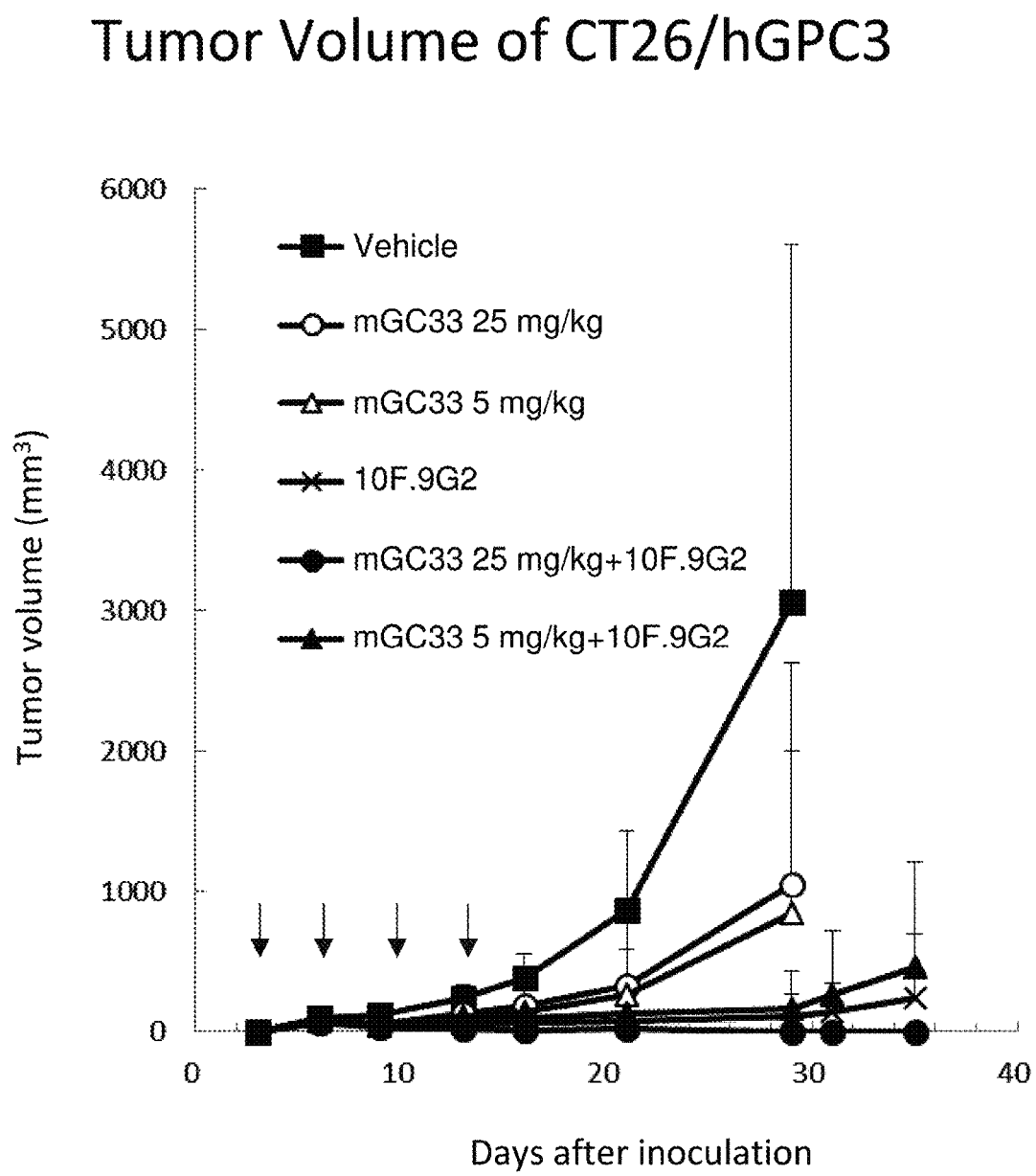
FIG. 3A is a diagram showing the CT26 expressing human GPC3 tumor volume changes in each mice treated either by monotherapy (mGC33 or 10F.9G2 (anti-PD-L1)) or combination (mGC33+10F.9G2). Arrow indicates date of the injection. Five mice per group were treated. Average of tumor volume in each group and SD bar were plotted.
Figure 3B:
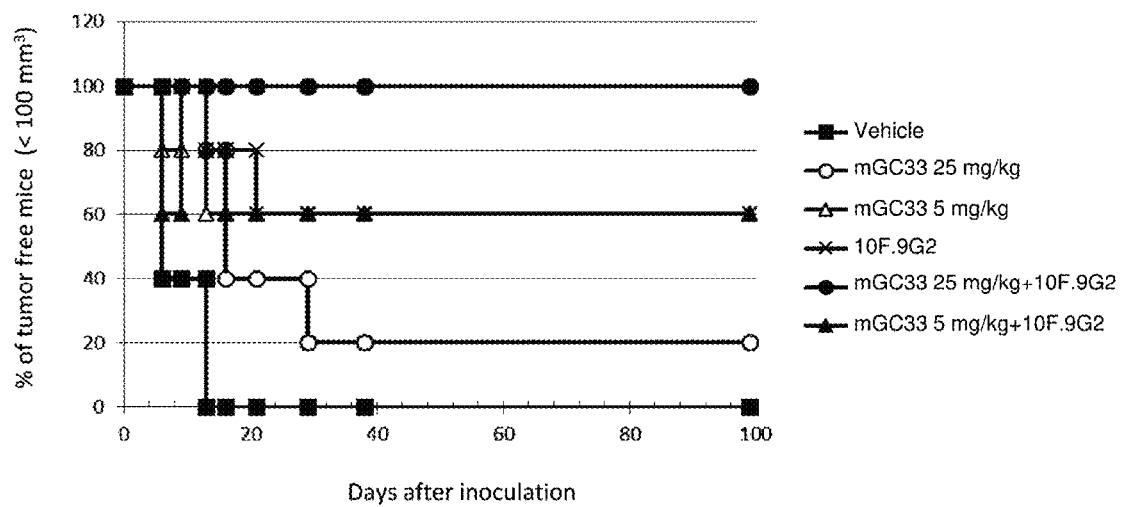
FIG. 3B is a diagram showing the progression free survival rate in CT26/hGPC3 bearing mice treated either by monotherapy (mGC33 or 10F.9G2 (anti-PD-L1)) or combination (mGC33+10F.9G2). Progression was defined when tumor size was reached more than 100 mm$^3$.
Figure 4A:
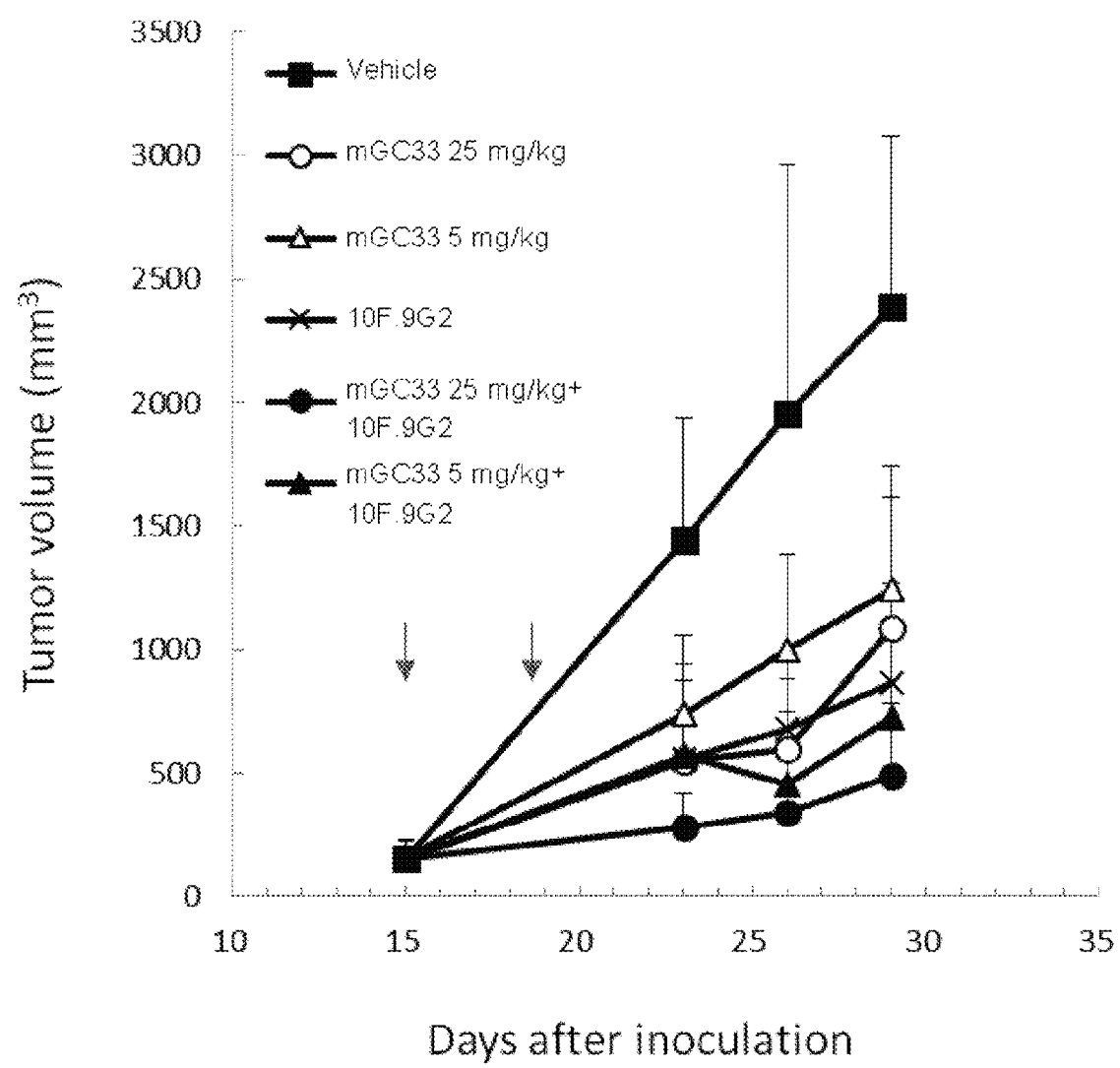
FIG. 4A is a diagram showing the CT26 expressing human GPC3 tumor volume changes in each mice treated either by monotherapy or combination. Arrow indicates date of the injection. Five mice per group were treated. Average of tumor volume in each group and SD bar were plotted. Tumor growth inhibition values of 5 mg/kg or 25 mg/kg of mGC33, 10F.9G2, 5 mg/kg or 25 mg/kg of mGC33+ 10F.9G2 were 52%, 58%, 68%, 75% and 85%, respectively.
Figure 4B:
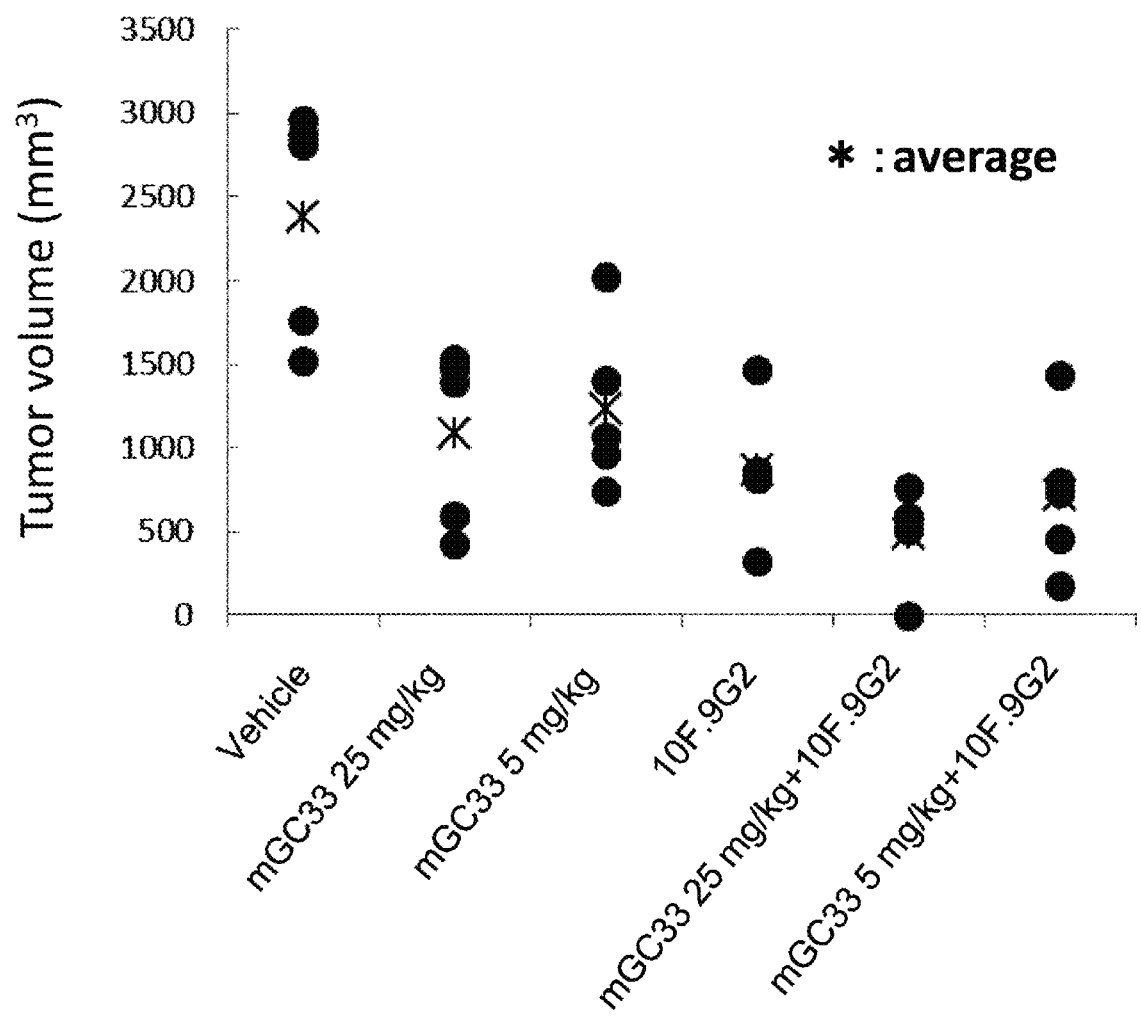
FIG. 4B is a diagram showing the individual tumor volume at day 29. Average (*) of tumor volume in each group was also plotted.

In both models, combination of 25 mg/kg of GC33 and 10F.9G2 showed most potent anti-tumor activity compared to those by each monotherapy (FIGS. 3 and 4).

Example 5

Anti-Tumor Activity in Combination with the Anti-GPC3 (GC33) and Anti-PD-L1 Antibodies (10F.9G2) in Syngenic Mouse Model Using Hepa1-6 Cell Line Expressing Human GPC3

Either 1, 5, or 25 mg/kg of mouse GC33 antibody once a week for 3 weeks or 200 µg of anti-mouse PD-L1 rat antibody, 10F.9G2 followed by 100 µg weekly for 2 weeks as a single agent or combination were injected intravenously to Hepa1-6 bearing mice as same as above. Pathological examination was conducted with HE staining sections which prepared with conventional methods described above. As to the IHC, 1st antibodies listed in the Table 2 were used for each markers and visualized either by LSAB methods described above or ENV+ method. IHC was conducted for 3 representative animals from each group.

TABLE 2

List of antibodies used in the IHC staining

| Marker | 1st Antibody | | Visualization system |
|---|---|---|---|
| | Clone/isotype | Source | |
| GPC3 | GC33/mouse IgG2a | in house | LSAB |
| PD1 | —/goat poly IgG | R&D Systems, Inc. | LSAB* |
| PD-L1 | —/goat poly IgG | R&D Systems, Inc. | LSAB* |
| F4/80 | CI:A3-1/rat IgG2b | BioLegend, Inc. | LSAB |
| CD204 | SRA-E5/mouse IgG1 | TransGenic, Inc. | LSAB |
| CD206 | MR5D3/rat IgG2a | GeneTex, Inc. | LSAB |
| CD163 | —/rabbit poly IgG | Santa Cruz Biotechnology, Inc. | ENV+ |
| CD11b | EPR1344/rabbit IgG | Novus Biologicals | ENV+ |
| CD11c | —/rabbit poly IgG | Proteintech | ENV+ |
| CD3 | SP7/rabbit IgG | GeneTex, Inc. | ENV+ |
| FoxP3 | FJK-16s/rat IgG2a | eBioscience, Inc. | LSAB |
| CD45R | RA3-6B2/rat IgG2a | Santa Cruz Biotechnology, Inc. | LSAB |
| ICOS | C398.4A/hamster IgG | BioLegend, Inc. | LSAB |
| CD34 | MEC14.7/rat IgG2a | BioLegend, Inc. | LSAB |

*Biotinylated Rabbit Anti-Goat IgG Antibody (Vector Laboratoties, Inc.)
LSAB, Streptavidin, Horseradish Peroxidase, R.T.U. (Vector Laboratoties, Inc. or Dako)
ENV+, EnVision+ System-HRP. Labelled Polymer. Anti-Rabbit (Dako)

Figure 5A:
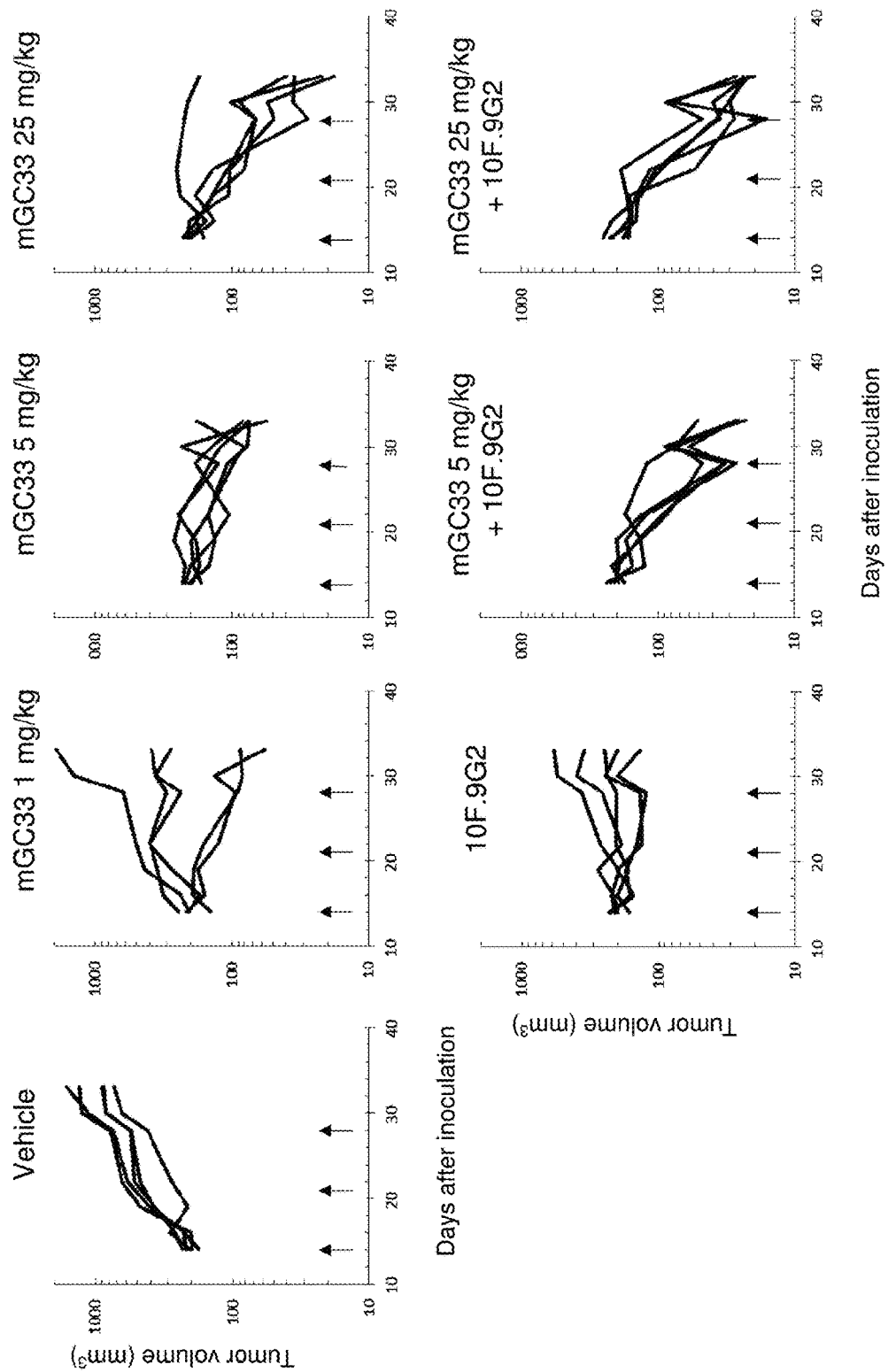
FIG. 5A is a diagram showing the Hepa1-6 expressing human GPC3 tumor volume changes in each mice treated either by vehicle control, 1 mg/kg, 5 mg/kg or 25 mg/kg of mGC33, 10F.9G2 or combination of 5 mg/kg or 25 mg/kg of GC33 and 10F.9G2. Arrow indicates date of the injection. Five mice per each group were treated.
Figure 5B:
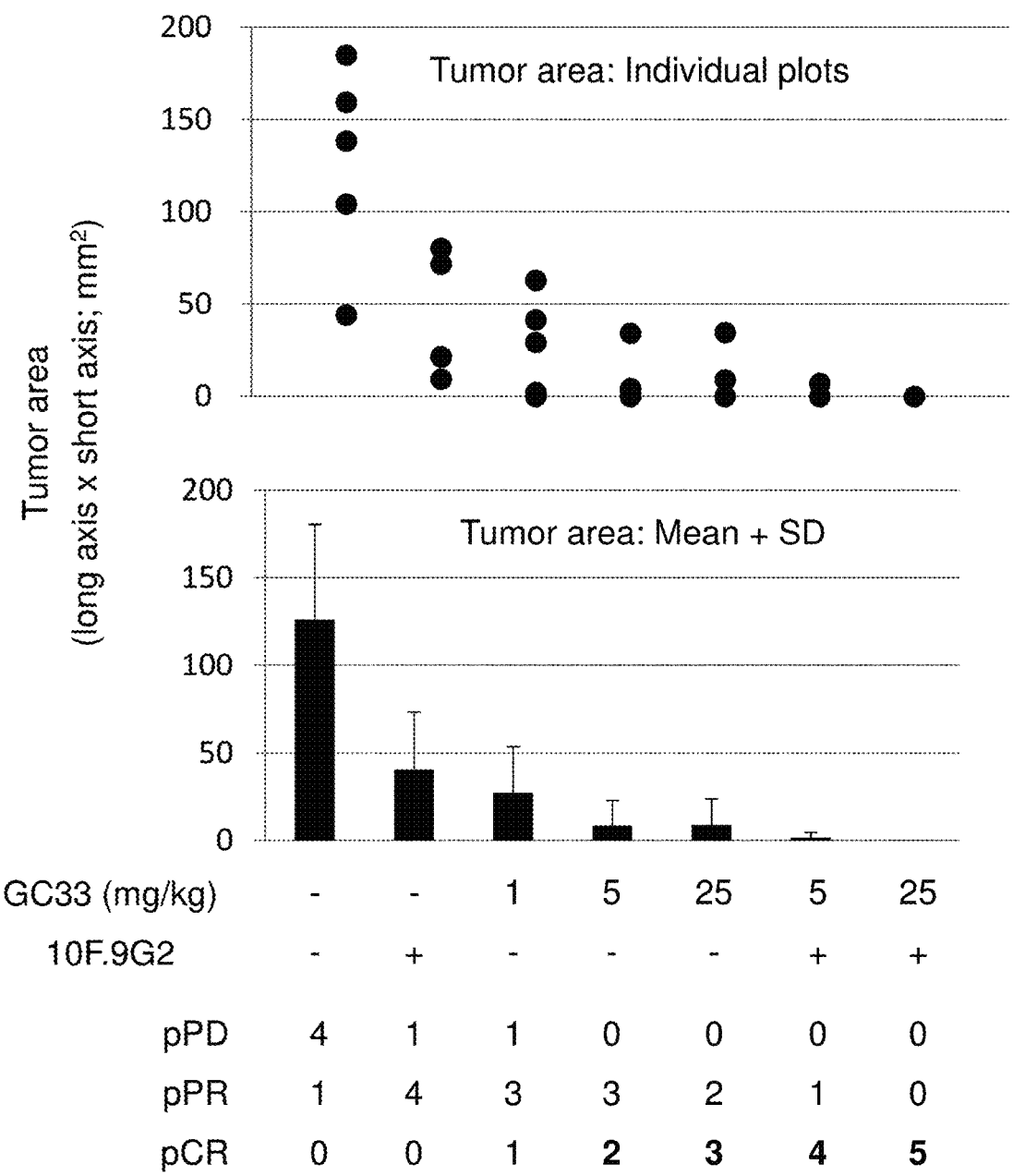
FIG. 5B is a diagram showing the individual tumor area or mean+SD of tumor area in each treated group at day 34. Tumor area (mm$^2$) was calculated by (length (mm) of long axis of tumor tissue)×(length (mm) of short axis of tumor tissue) after HE staining of tumor tissues isolated from each mice. And the results of pathological evaluation of each tumor tissues were added in the bottom of graphs. Pathological progression of disease (pPD) was defined as "no tumor regression was noted". Pathological partial regression (pPR) was defined as "degeneration and/or necrosis of tumor cells with immune cell infiltration was noted". Pathological complete regression (pCR) was defined as "no tumor cells were noted in the tumor implantation site".

While mouse GC33 or 10F.9G2 showed inhibition of tumor growth compared to vehicle control, mouse GC33 and 10F.9G2 combination showed the strongest anti-tumor activity (FIG. 5A). Five days after 3rd injection, all mice were necropsied and tumor tissues were evaluated pathologically. In tumor tissues examined, no viable tumor cells were observed in all mice treated with 25 mg/kg of mouse GC33 in combination with PD-L1 antibody and in 4 out of 5 mice treated with 5 mg/kg of mouse GC33 in combination with PD-L1 antibody (FIG. 5B).

Pathological examination of each treated tumor tissues revealed that increase in number of F4/80-positive cells, PD-L1 expression on the multinucleated giant cells (MNGC) and CD3-positive cells infiltrated into tumor tissues and decrease in number of CD206, CD163, and CD11b-positive cells (MNC) and PD-L1 expression on the mononuclear cells (MNC) by each treatments compared to vehicle control. By combination, infiltration of CD3-positive T cells was increased than each monotherapy which tend to be related to anti-tumor activities (Table 3).

TABLE 3

Pathological evaluations of treated tumors

| | Vehicle (n = 3) | mGC33 5 mg/kg (n = 3) | mGC33 1 mg/kg (n = 3) | 10F.9G2 (n = 3) | mGC33 5 mg/kg + 10F.9G2 (n = 3) |
|---|---|---|---|---|---|
| Tumor cell | | | | | |
| GPC3 | 3* | 2 | 1~3 | 2 | —~1 |
| PD1 | 1 | —~1 | 1~2 | —~1 | ' |
| PD-L1 | 2 | 1~2 | 1~2 | 1~2 | 1 |
| Immune cell infiltration | | | | | |
| F4/80 | 3 | 3~4 | 3~4 | 3~4 | 3~4 |
| CD204 | 3 | 3~4 | 3~4 | 3~4 | 3~4 |
| CD206 | 2 | 1 | 1 | 1 | —~1 |
| CD163 | 2 | 1~2 | 1~2 | 1 | 1 |
| CD11b | 3 | 2 | 3 | 2 | 2 |

TABLE 3-continued

Pathological evaluations of treated tumors

| | Vehicle (n = 3) | mGC33 5 mg/kg (n = 3) | mGC33 1 mg/kg (n = 3) | 10F.9G2 (n = 3) | mGC33 5 mg/kg + 10F.9G2 (n = 3) |
|---|---|---|---|---|---|
| CD11c | 1~2 | 1~2 | 1 | 1~2 | 2 |
| CD3 | 2 | 2~3 | 1~2 | 2~3 | 3 |
| FoxP3 | 1 | 1 | ' | ' | 1 |
| B220 | 1 | 1 | ' | ' | 1 |
| ICOS | 1 | 1~2 | ' | 1~2 | 1~2 |
| PD1 | 2 | 2 | 1~2 | 1 | 1~2 |
| PD-L1(MNC) | 2 | 1~2 | 1 | 1 | 1 |
| PD-L1 (MNGC) | 1 | 1~3 | —~3 | 2~3 | 1~3 |
| Vasculature | | | | | |
| CD34 | 3 | 1 | 1 | 1 | 1 |

MNC mononuclear cell; MNGC multinucleated giant cell
*Severity of lesion: 1. Very slight; 2. Slight; 3. Moderate; 4. Marked.

Example 6

Anti-Tumor Activity in Combination with the Anti-GPC3 (GC33) and Anti-PD-L1 Antibodies (6E11) in Syngenic Mouse Model Using Hepa1-6 Cell Line Expressing Human GPC3

Mouse GC33 at 1 mg/kg or 5 mg/kg was given intravenously once or three times for weekly (q7d x 3) to C57BL/6J mice with established Hepa1-6/hGPC3 tumors. Anti-mouse PD-L1 mAb (clone 6E11, mIgG2A, D265A and N297A; Genentech [WO2015/0954181] at 10 mg/kg intravenously once followed by 5 mg/kg intraperitoneal two times weekly (q7d x 3) was given.

Figure 6A:
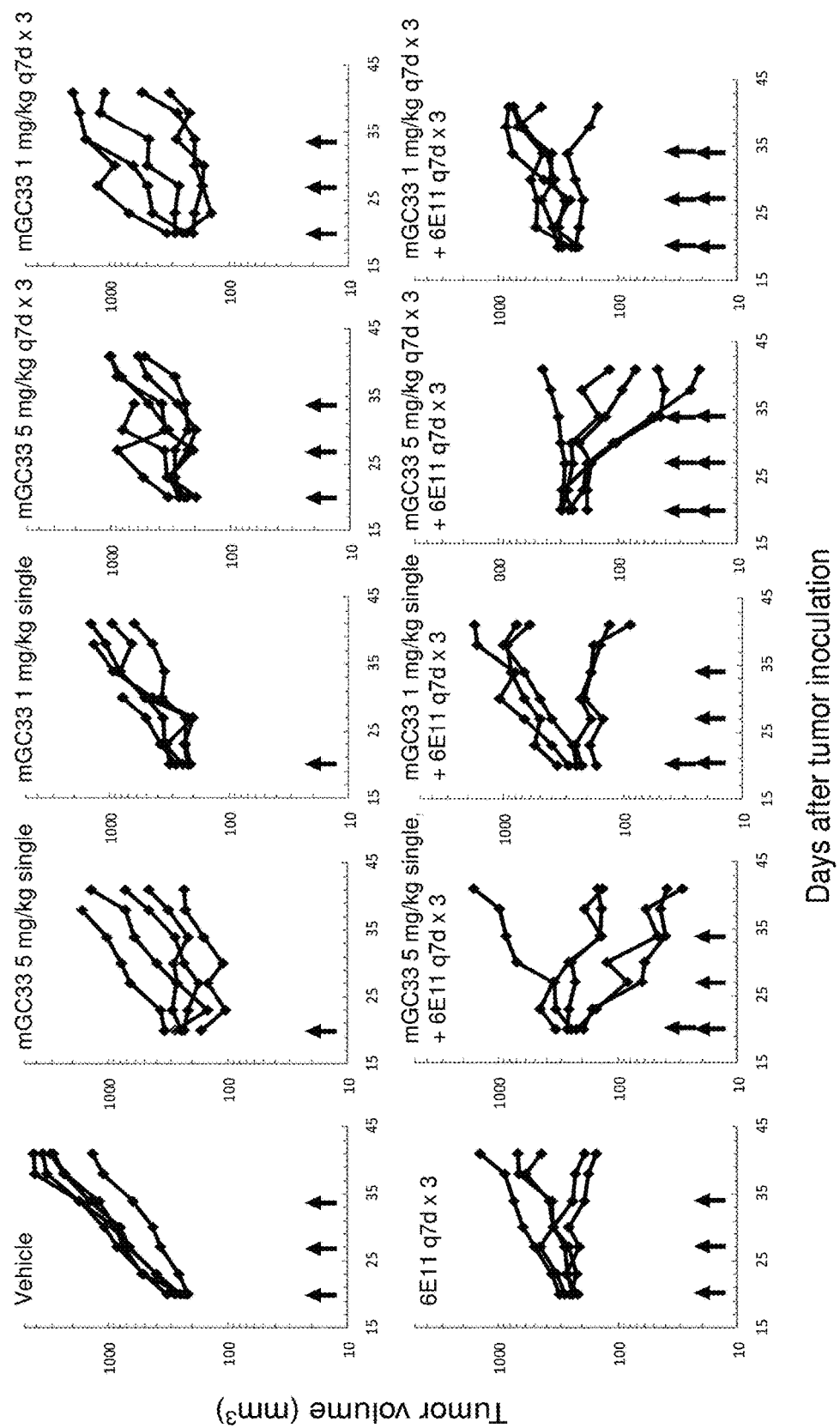
FIG. 6A is a diagram showing the Hepa1-6 expressing human GPC3 tumor volume changes in each mice treated either by monotherapy or combination of mGC33 and 6E11 (anti-PD-L1) with various dose levels and schedules indicated. Arrow indicates date of the injection. Five mice per each group were treated.
Figure 6B:
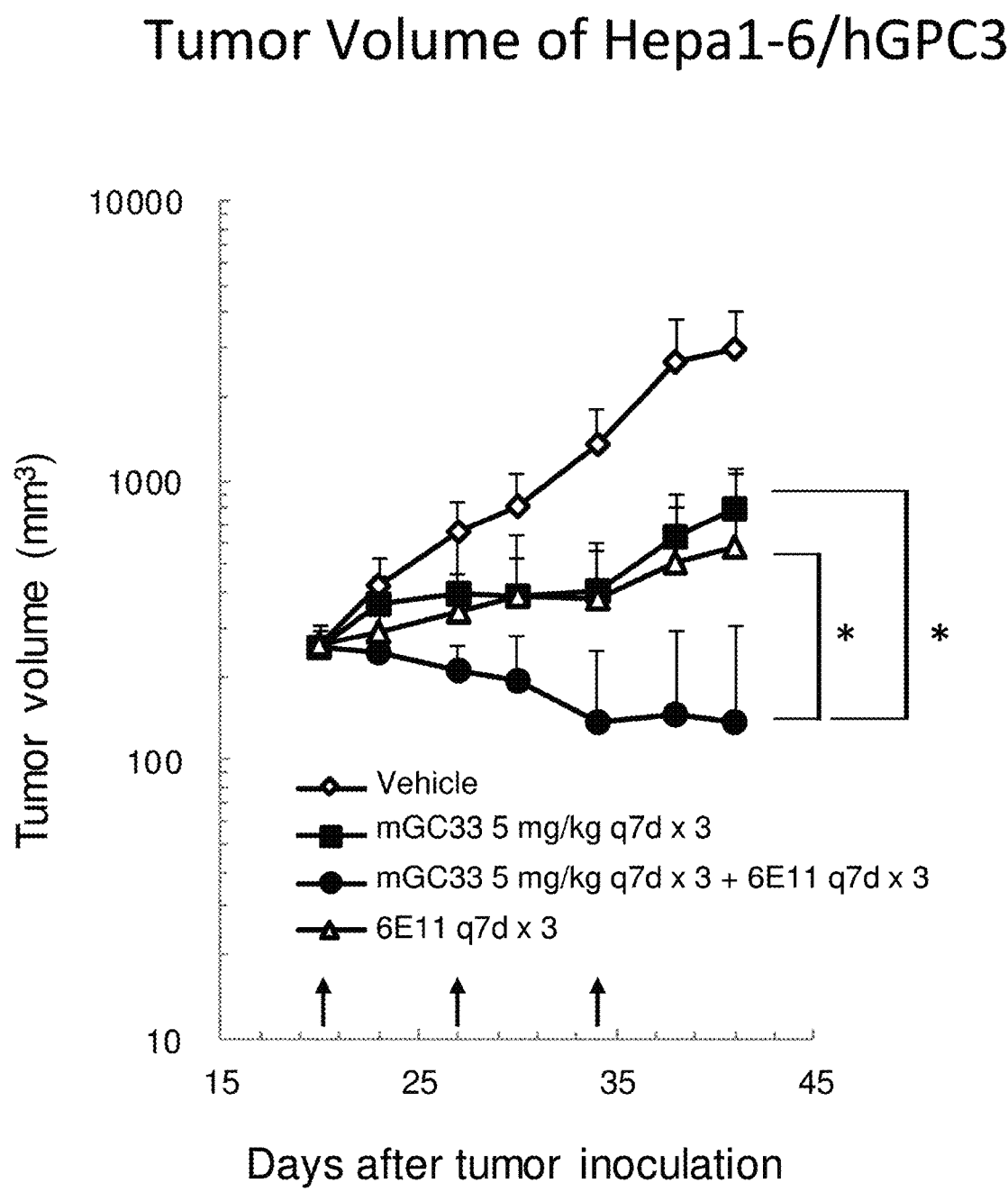
FIG. 6B is a diagram showing the mean values of the Hepa1-6 expressing human GPC3 tumor volume changes in each mice group treated either by monotherapy or combination of mGC33 and 6E11. Tumor growth in the combination group was significantly inhibited compared with those in the groups treated either by GC33 or 6E11 monotherapy. Arrow indicates date of the injection. Five mice per each group were treated. *: P<0.05 by Wilcoxon (SAS Institute Inc.).

The combination therapy increased inhibition of tumor growth compared with treatment with either monotherapy (FIG. 6A, B). Final measurements of the tumor growth inhibition values of 1 mg/kg mGC33 single, 5 mg/kg mGC33 single, 1 mg/kg mGC33 q7dx3, 5 mg/kg mGC33 q7dx3, 6E11 q7dx3, 6E11 q7dx3+1 mg/kg mGC33 single, 6E11 q7dx3+5 mg/kg mGC33 single, and 6E11 q7dx3+1 mg/kg mGC33 q7dx3, 6E11 q7dx3+5 mg/kg mGC33 q7dx3 were respectively 73%, 84%, 73%, 80%, 88%, 85%, 95%, 88%, and 104%. One mouse in the 5 mg/kg mGC33 q7dx3 group, one mouse in the 1 mg/kg mGC33 q7dx3 group, one mouse in the 5 mg/kg mGC33 single, two mice in the 1 mg/kg mGC33 single group were euthanized by tumor progression. None of the mice died and no severe weight loss was observed during the administration period (FIG. 6C).

Figure 7:
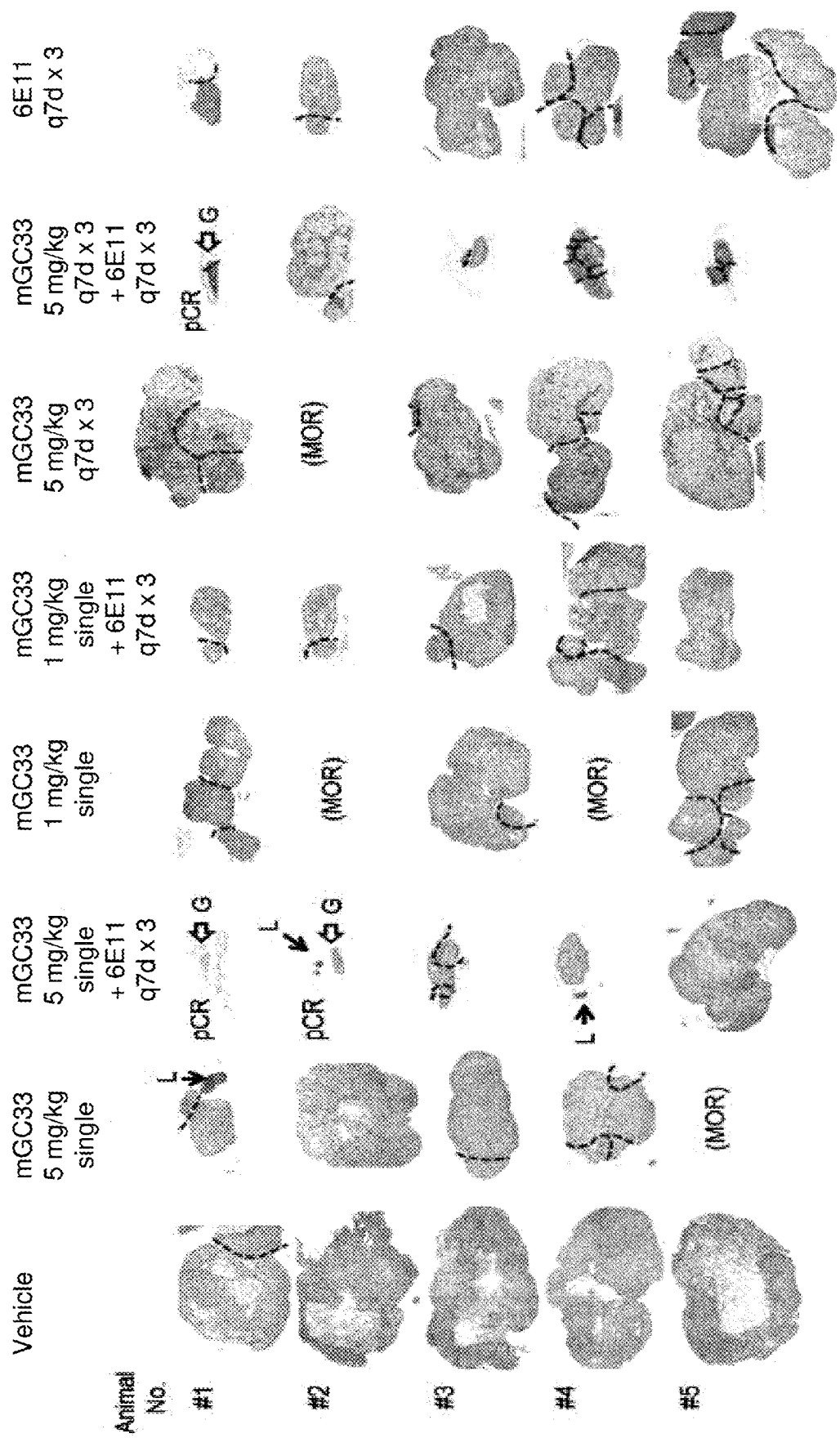
FIG. 7 is a diagram showing photomicrographs of tumor tissues in subcutis in each group. Gray area indicates the tumor area or lymphoid/granulation tissues whithout necrosis. Blue area indicates the tumor area or granulation tissue with necrosis. Dotted line indicates the border of mass. L stands for the lymphoid tissue, G stands for granulation tissue, pCR stands for pathological complete response (no tumor tissue on the histopathology slide), and MOR stands for moribund sacrifice animal caused by tumor progression.
Figure 8A:
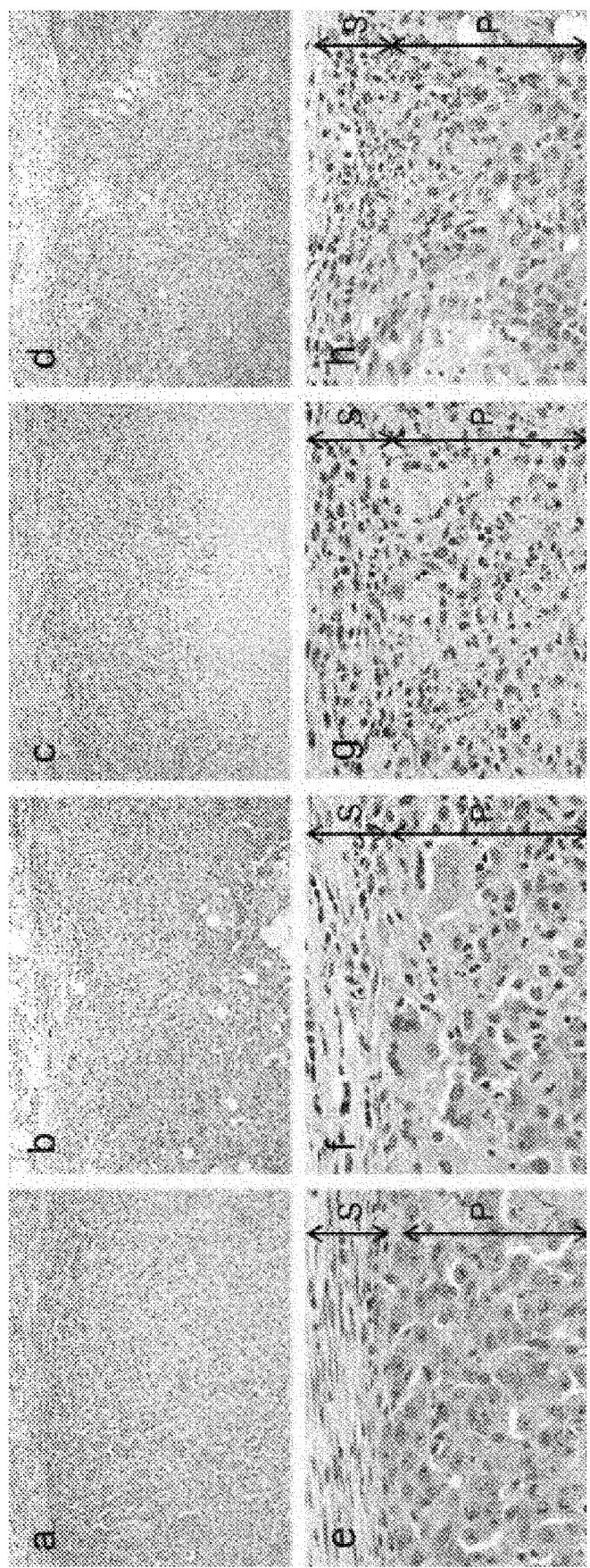
FIG. 8A is a diagram showing representative photomicrographs of HE stained tumor tissues in periphery of mass adjusting to stroma in each treated groups. Necrosis of tumor with infiltration of immune cells including macrophages/ multinucleated giant cells are noted in all treated groups. Severity of lesions is following order: mGC33 5 mg/kg single+6E11 q7d×3>mGC33 5 mg/kg single or 6E11 q7d×3. S stands for stroma adjusting tumor mass, and P stands for periphery of tumor mass.
Figure 8B:
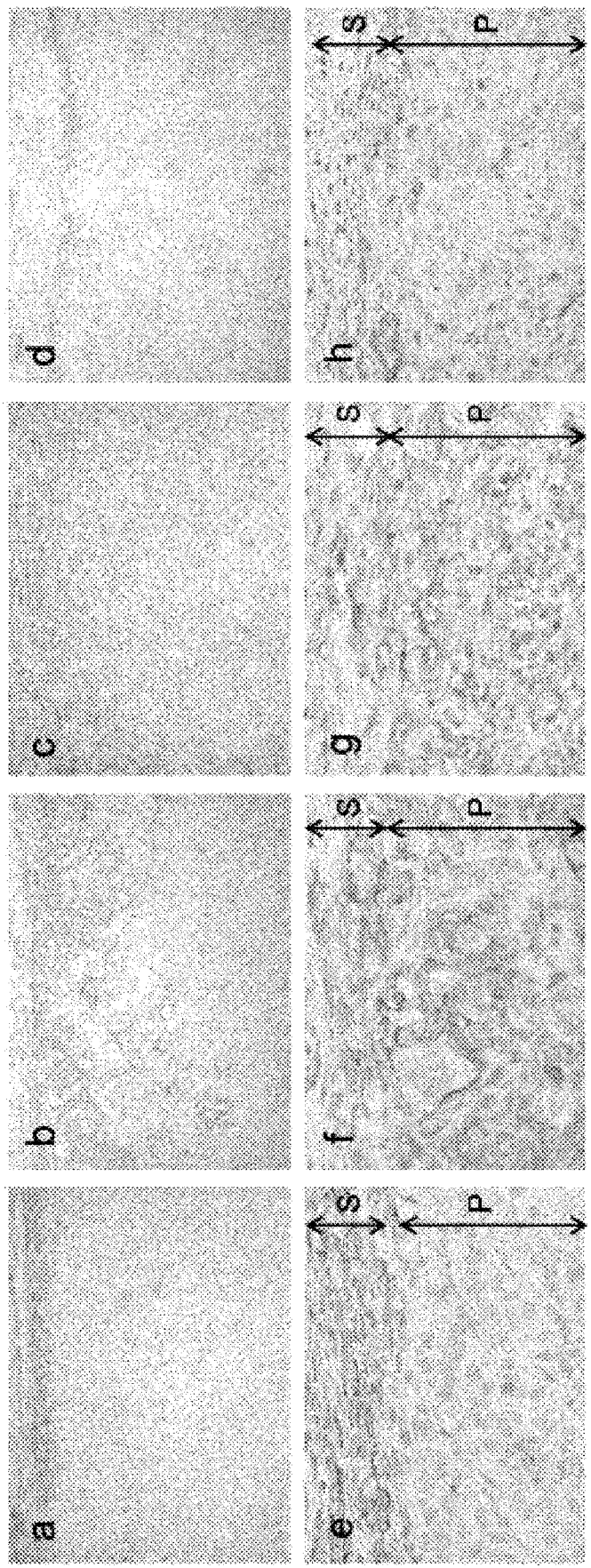
FIG. 8B is a diagram showing representative photomicrographs of F4/80 IHC of tumor tissues in periphery of mass adjusting to stroma in each treated groups. In vehicle, F4/80-positive cells are mainly noted in stroma. On the other hand, increased severity of F4/80-positive immune cells including macrophages/multinucleated giant cells are noted mainly in periphery of tumor mass in all treated groups. Severity of positive cell infiltration is following order: mGC33 5 mg/kg single+6E11 q7d×3>mGC33 5 mg/kg single or 6E11 q7d×3. S stands for stroma adjusting tumor mass, and P stands for periphery of tumor mass.
Figure 8C:
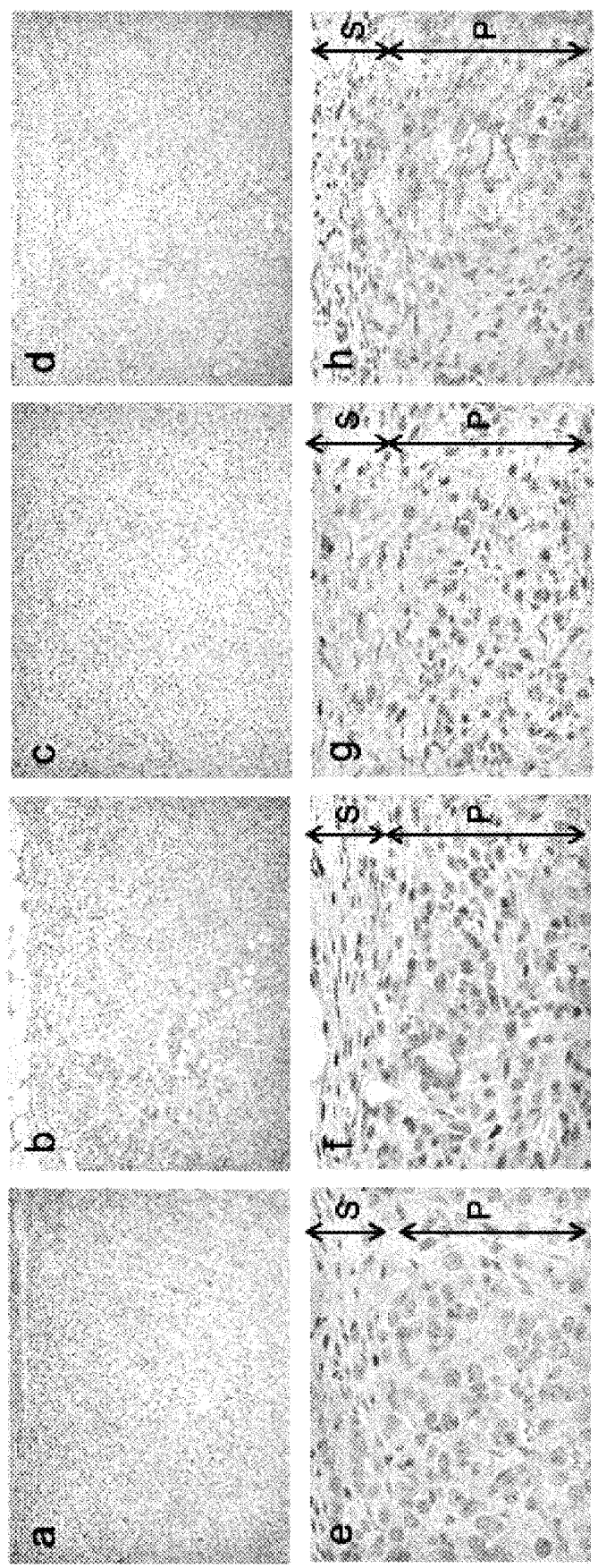
FIG. 8C is a diagram showing representative photomicrographs of PD-L1 IHC of tumor tissues in periphery of mass adjusting to stroma in each treated groups. In vehicle, PD-L1-positive reactions are mainly noted in cytoplasm of tumor cells with weak intensity. On the other hand, increased severity of PD-L1-positive reactions in immune cells including macrophages/multinucleated giant cells are noted with weak to medium intensity in all treated groups. S stands for stroma adjusting tumor mass, and P stands for periphery of tumor mass.

From the result of histopathology, decreased tumor area accompanying with or without increased severity of necrosis was observed by administration of mGC33, 6E11 and the combination (FIG. 7). In the 6E11 q7dx3+5 mg/kg mGC33 single or q7dx3 groups, the pathological complete responses (pCR; no tumor tissues on the histopathology slide) were observed in one or two out of five mice. Furthermore, necrosis of tumor with infiltration of immune cells including macrophages/multinucleated giant cells were noted in all treated groups; severity of lesions were following order: mGC33 5 mg/kg single or q7dx3, 6E11 q7dx3<mGC33 5 mg/kg single or q7dx3+6E11 q7dx3 (FIG. 8A). As shown in FIG. 8B, F4/80 positive cells observed in the periphery of tumor mass were most abundant in combination cases, then mGC33 or 6E11 q7dx3 and vehicle in this order (FIG. 8B). In vehicle, PD-L1-positive reactions were mainly noted in cytoplasm of tumor cells with weak intensity. On the other hand, increased intensity (weak to medium) and frequency of PD-L1-positive reactions in immune cells including macrophages/multinucleated giant cells were noted in all treated groups (FIG. 8C).

Example 7

Induction of Cytotoxic T Cells in Syngenic Mouse Model Using Hepa1-6 Cell Line Expressing Human GPC3

In addition to the innate immunity by NK cells and macrophage, induction of acquired immunity by cytotoxic T cells is important to kill tumor cells. To assess the induction of acquired immunity in the mice treated, infiltrated T cells into tumor tissues were evaluated. Hepa1-6 cells expressing human GPC3 were inoculated subcutaneously into C57BL/6J mice. Once palpable tumors were established, mice were allocated into 12 groups; 3 groups were as control, 3 groups were treated by 5 mg/kg of mouse GC33 for 2 times at day 13 and 20 after tumor inoculation, 3 groups were treated by 10 mg/kg of 6E11 at day 13 and 5 mg/kg of 6E11 at day 20 after tumor inoculation, or 3 groups were treated in combination of mouse GC33 (2 times at day 13 and 20 after tumor inoculation) and 6E11 (10 mg/kg of 6E11 at day 13 and 5 mg/kg of 6E11 at day 20 after tumor inoculation). After 1, 3 and 8 days from the 2nd administration, tumor tissues were isolated and minced. After digestion by gentleMACS(trade mark) Octo Dissociator, cells were washed and used for the flowcytometry to quantify the CD45, CD3c, CD4 or CD8 positive tumor infiltrated lymphocytes (TILs).

Figure 9:
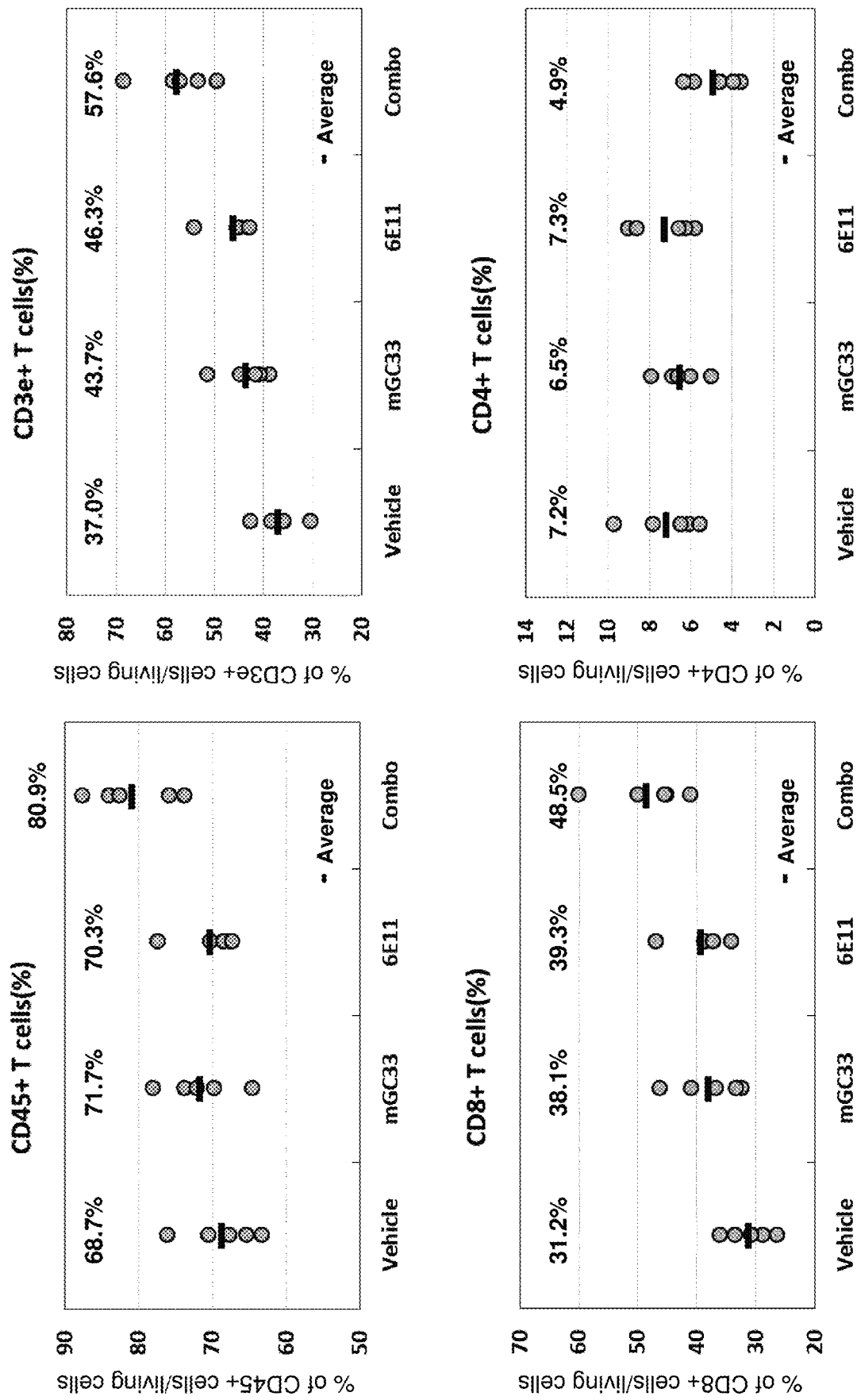
FIG. 9 is a diagram showing the percentage of marker positive cells observed in tumor tissues in each treated groups. Individual values and average in each groups are plotted and average values are indicated in each graphs.

As shown in FIG. 9, in mice treated either with mouse GC33 or 6E11, increase of CD45-positive lymphocytes, CDR-positive and CD8-positive T lymphocytes but not CD4-positive lymphocytes were observed. As same as anti-tumor activities described above, in combination of mouse GC33 and 6E11, stronger induction of lymphocytes including CD8-positive TILs observed than each monotherapy.

INDUSTRIAL APPLICABILITY

The present invention contributes to improvement in the efficacy of a PD-1 axis binding antagonist or an anti-GPC3 antibody by combining each other and improvement in QOL of a patient to be treated, and is useful in the treatment of cancer including liver cancer.

The invention claimed is:

1. A method for treating or delaying progression of cancer in an individual, comprising administering a therapeutically effective amount of an anti-GPC3 antibody to the individual, wherein the individual is also being administered atezolizumab, wherein the anti-GPC3 antibody comprises a heavy chain comprising HVR-H1 sequence of SEQ ID NO:42, HVR-H2 sequence of SEQ ID NO: 43, and HVR-H3 sequence of SEQ ID NO: 44; and a light chain comprising HVR-L1 sequence of SEQ ID NO: 45, HVR-L2 sequence of SEQ ID NO: 46, and HVR-L3 sequence of SEQ ID NO: 47, and wherein the cancer is liver cancer.

2. The method according to claim 1 wherein the anti-GPC3 antibody is a humanized antibody.

3. The method according to claim 2, wherein the anti-GPC3 antibody comprises a heavy chain variable region comprising the amino acid sequence of SEQ ID NO:50 and a light chain variable region comprising the amino acid sequence of SEQ ID NO:52.

4. The method according to claim 1, wherein the cancer is selected from the group consisting of liver cancer, breast cancer, lung cancer, ovarian cancer, gastric cancer, bladder cancer, pancreatic cancer, endometrial cancer, colon cancer, kidney cancer, esophageal cancer and prostate cancer.

5. A method for treating or delaying progression of cancer in an individual, comprising administering to the individual a therapeutically effective amount of an anti-GPC3 antibody, and administering a therapeutically effective amount of atezolizumab, wherein the anti-GPC3 antibody comprises a heavy chain comprising HVR-H1 sequence of SEQ ID NO:42, HVR-H2 sequence of SEQ ID NO: 43, and HVR-H3 sequence of SEQ ID NO: 44; and a light chain comprising HVR-L1 sequence of SEQ ID NO: 45, HVR-L2 sequence of SEQ ID NO: 46, and HVR-L3 sequence of SEQ ID NO: 47, and wherein the cancer is liver cancer.

6. A method for treating or delaying progression of cancer in an individual, comprising administering a therapeutically effective amount of atezolizumab to the individual, wherein the individual is also being administered a therapeutically effective amount of an anti-GPC3 antibody, wherein the anti-GPC3 antibody comprises a heavy chain comprising HVR-H1 sequence of SEQ ID NO:42, HVR-H2 sequence of SEQ ID NO: 43, and HVR-H3 sequence of SEQ ID NO: 44; and a light chain comprising HVR-L1 sequence of SEQ ID NO: 45, HVR-L2 sequence of SEQ ID NO: 46, and HVR-L3 sequence of SEQ ID NO: 47, and wherein the cancer is liver cancer.

7. The method according to claim 5 wherein the anti-GPC3 antibody is a humanized antibody.

8. The method according to claim 6 wherein the anti-GPC3 antibody is a humanized antibody.

* * * * *

SEQUENCE LISTING

```
<160> NUMBER OF SEQ ID NOS: 55

<210> SEQ ID NO 1
<211> LENGTH: 440
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205
```

Lys Arg Val Glu Ser Lys Tyr Gly Pro Pro Cys Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
                275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 118
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 4
<211> LENGTH: 108
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95
```

Thr Phe Gly Gln Gly Thr Lys Val Glu Ile Lys Arg
            100                 105

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asp or Gly

<400> SEQUENCE: 5

Gly Phe Thr Phe Ser Xaa Ser Trp Ile His
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Leu
<220> FEATURE:
<221> NAME/KEY: VARIANT
<222> LOCATION: 10
<223> OTHER INFORMATION: Xaa = Thr or Ser

<400> SEQUENCE: 6

Ala Trp Ile Xaa Pro Tyr Gly Gly Ser Xaa Tyr Tyr Ala Asp Ser Val
1               5                   10                  15

Lys Gly

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Arg His Trp Pro Gly Gly Phe Asp Tyr
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 9
<211> LENGTH: 13
<212> TYPE: PRT
<213> ORGANISM: Artificial Sequence
<220> FEATURE:

```
<223> OTHER INFORMATION: Synthetic Construct

<400> SEQUENCE: 9

Trp Val Arg Gln Ala Pro Gly Lys Gly Leu Glu Trp Val
1               5                   10

<210> SEQ ID NO 10
<211> LENGTH: 32
<212> TYPE: PRT
<213> ORGANISM: Artificial Sequence
<220> FEATURE:
<223> OTHER INFORMATION: Synthetic Construct

<400> SEQUENCE: 10

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Trp Gly Gln Gly Thr Leu Val Thr Val Ser Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Asp or Val
<220> FEATURE:
<221> NAME/KEY: VARIANT
<222> LOCATION: 6
<223> OTHER INFORMATION: Xaa = Val or Ile
<220> FEATURE:
<221> NAME/KEY: VARIANT
<222> LOCATION: 7
<223> OTHER INFORMATION: Xaa = Ser or Asn
<220> FEATURE:
<221> NAME/KEY: VARIANT
<222> LOCATION: 9
<223> OTHER INFORMATION: Xaa = Ala or Phe
<220> FEATURE:
<221> NAME/KEY: VARIANT
<222> LOCATION: 10
<223> OTHER INFORMATION: Xaa = Val or Leu

<400> SEQUENCE: 12

Arg Ala Ser Gln Xaa Xaa Xaa Thr Xaa Xaa Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
```

```
<223> OTHER INFORMATION: Xaa = Phe or Thr
<220> FEATURE:
<221> NAME/KEY: VARIANT
<222> LOCATION: 6
<223> OTHER INFORMATION: Xaa = Tyr or Ala

<400> SEQUENCE: 13

Ser Ala Ser Xaa Leu Xaa Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Tyr, Gly, Phe or Ser
<220> FEATURE:
<221> NAME/KEY: VARIANT
<222> LOCATION: 4
<223> OTHER INFORMATION: Xaa = Leu, Tyr, Phe or Trp
<220> FEATURE:
<221> NAME/KEY: VARIANT
<222> LOCATION: 5
<223> OTHER INFORMATION: Xaa = Tyr, Asn, Ala, Thr, Gly, Phe or Ile
<220> FEATURE:
<221> NAME/KEY: VARIANT
<222> LOCATION: 6
<223> OTHER INFORMATION: Xaa = His, Val, Pro, Thr or Ile
<220> FEATURE:
<221> NAME/KEY: VARIANT
<222> LOCATION: 8
<223> OTHER INFORMATION: Xaa = Ala, Trp, Arg, Pro or Thr

<400> SEQUENCE: 14

Gln Gln Xaa Xaa Xaa Xaa Pro Xaa Thr
1               5

<210> SEQ ID NO 15
<211> LENGTH: 23
<212> TYPE: PRT
<213> ORGANISM: Artificial Sequence
<220> FEATURE:
<223> OTHER INFORMATION: Synthetic Construct

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Artificial Sequence
<220> FEATURE:
```

```
<223> OTHER INFORMATION: Synthetic Construct

<400> SEQUENCE: 17

Gly Val Pro Ser Arg Phe Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Phe Gly Gln Gly Thr Lys Val Glu Ile Lys Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Gly Phe Thr Phe Ser Asp Ser Trp Ile His
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Ala Trp Ile Ser Pro Tyr Gly Gly Ser Thr Tyr Tyr Ala Asp Ser Val
1               5                   10                  15

Lys Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Arg His Trp Pro Gly Gly Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Arg Ala Ser Gln Asp Val Ser Thr Ala Val Ala
1               5                   10

<210> SEQ ID NO 23
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Ser Ala Ser Phe Leu Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gln Gln Tyr Leu Tyr His Pro Ala Thr
1               5

<210> SEQ ID NO 25
<211> LENGTH: 118
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 26
<211> LENGTH: 122
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60
```

-continued

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Trp Gly Gln Gly Thr Leu Val Thr Val Ser Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Phe Gly Gln Gly Thr Lys Val Glu Ile Lys
1               5                   10

<210> SEQ ID NO 29
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Trp Val Arg Gln Ala Pro Gly Lys Gly Leu Glu Trp Val Ala
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Synthetic Construct

<400> SEQUENCE: 31

Trp Gly Gln Gly Thr Leu Val Thr Val Ser Ser Ala Ser Thr Lys
```

<210> SEQ ID NO 32
<211> LENGTH: 447
<212> TYPE: PRT
<213> ORGANISM: Artificial Sequence
<220> FEATURE:
<223> OTHER INFORMATION: Synthetic Construct

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

```
                355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
        420                 425                 430
Leu His Asn His Tyr Thr Gln Lys Ser Leu Ser Leu Ser Pro Gly
                435                 440                 445

<210> SEQ ID NO 33
<211> LENGTH: 214
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Leu Tyr His Pro Ala
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 34
<211> LENGTH: 5
<212> TYPE: PRT
<213> ORGANISM: Mus musculus

<400> SEQUENCE: 34

Asp Tyr Ser Met His
1               5
```

```
<210> SEQ ID NO 35
<211> LENGTH: 17
<212> TYPE: PRT
<213> ORGANISM: Mus musculus

<400> SEQUENCE: 35

Trp Ile Asn Thr Glu Thr Gly Glu Pro Thr Tyr Ala Asp Asp Phe Lys
1               5                   10                  15

Gly

<210> SEQ ID NO 36
<211> LENGTH: 2
<212> TYPE: PRT
<213> ORGANISM: Mus musculus

<400> SEQUENCE: 36

Leu Tyr
1

<210> SEQ ID NO 37
<211> LENGTH: 16
<212> TYPE: PRT
<213> ORGANISM: Mus musculus

<400> SEQUENCE: 37

Lys Ser Ser Gln Ser Leu Leu His Ser Asp Gly Lys Thr Phe Leu Asn
1               5                   10                  15

<210> SEQ ID NO 38
<211> LENGTH: 7
<212> TYPE: PRT
<213> ORGANISM: Mus musculus

<400> SEQUENCE: 38

Leu Val Ser Arg Leu Asp Ser
1               5

<210> SEQ ID NO 39
<211> LENGTH: 9
<212> TYPE: PRT
<213> ORGANISM: Mus musculus

<400> SEQUENCE: 39

Cys Gln Gly Thr His Phe Pro Arg Thr
1               5

<210> SEQ ID NO 40
<211> LENGTH: 111
<212> TYPE: PRT
<213> ORGANISM: Mus musculus

<400> SEQUENCE: 40

Gln Ile Gln Leu Glu Gln Ser Gly Pro Glu Leu Lys Lys Pro Gly Glu
1               5                   10                  15

Thr Val Lys Ile Ser Cys Lys Ala Ser Gly Tyr Ile Phe Arg Asp Tyr
                20                  25                  30

Ser Met His Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
```

```
                65                  70                  75                  80
Leu Gln Ile Asn Asn Leu Lys Asn Glu Asp Thr Ala Thr Tyr Phe Cys
                    85                  90                  95
Thr Ser Leu Tyr Trp Gly Gln Gly Thr Leu Val Thr Val Ser Ala
                100                 105                 110

<210> SEQ ID NO 41
<211> LENGTH: 112
<212> TYPE: PRT
<213> ORGANISM: Mus musculus

<400> SEQUENCE: 41

Asp Val Val Met Thr Gln Thr Pro Leu Thr Leu Ser Val Thr Leu Gly
1               5                   10                  15
Gln Pro Ala Ser Ile Ser Cys Lys Ser Ser Gln Ser Leu Leu His Ser
            20                  25                  30
Asp Gly Lys Thr Phe Leu Asn Trp Leu Leu Gln Arg Pro Gly Gln Ser
        35                  40                  45
Pro Lys Arg Leu Ile Tyr Leu Val Ser Arg Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Cys Gln Gly
                85                  90                  95
Thr His Phe Pro Arg Thr Phe Gly Gly Gly Thr Arg Leu Glu Ile Lys
                100                 105                 110

<210> SEQ ID NO 42
<211> LENGTH: 5
<212> TYPE: PRT
<213> ORGANISM: Mus musculus

<400> SEQUENCE: 42

Asp Tyr Glu Met His
1               5

<210> SEQ ID NO 43
<211> LENGTH: 17
<212> TYPE: PRT
<213> ORGANISM: Mus musculus

<400> SEQUENCE: 43

Ala Leu Asp Pro Lys Thr Gly Asp Thr Ala Tyr Ser Gln Lys Phe Lys
1               5                   10                  15
Gly

<210> SEQ ID NO 44
<211> LENGTH: 6
<212> TYPE: PRT
<213> ORGANISM: Mus musculus

<400> SEQUENCE: 44

Phe Tyr Ser Tyr Thr Tyr
1               5

<210> SEQ ID NO 45
<211> LENGTH: 16
<212> TYPE: PRT
<213> ORGANISM: Mus musculus

<400> SEQUENCE: 45
```

Arg Ser Ser Gln Ser Leu Val His Ser Asn Arg Asn Thr Tyr Leu His
1               5                   10                  15

<210> SEQ ID NO 46
<211> LENGTH: 7
<212> TYPE: PRT
<213> ORGANISM: Mus musculus

<400> SEQUENCE: 46

Lys Val Ser Asn Arg Phe Ser
1               5

<210> SEQ ID NO 47
<211> LENGTH: 9
<212> TYPE: PRT
<213> ORGANISM: Mus musculus

<400> SEQUENCE: 47

Ser Gln Asn Thr His Val Pro Pro Thr
1               5

<210> SEQ ID NO 48
<211> LENGTH: 115
<212> TYPE: PRT
<213> ORGANISM: Mus musculus

<400> SEQUENCE: 48

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val His Gly Leu Lys Trp Ile
        35                  40                  45

Gly Ala Leu Asp Pro Lys Thr Gly Asp Thr Ala Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ala
        115

<210> SEQ ID NO 49
<211> LENGTH: 112
<212> TYPE: PRT
<213> ORGANISM: Mus musculus

<400> SEQUENCE: 49

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Leu Gly Val Tyr Phe Cys Ser Gln Asn
                    85                  90                  95

Thr His Val Pro Pro Thr Phe Gly Ser Gly Thr Lys Leu Glu Ile Lys
                    100                 105                 110

<210> SEQ ID NO 50
<211> LENGTH: 115
<212> TYPE: PRT
<213> ORGANISM: Artificial Sequence
<220> FEATURE:
<223> OTHER INFORMATION: modified antibody fragment

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Trp Gly Gln Gly Thr Leu Val Thr
                100                 105                 110

Val Ser Ser
        115

<210> SEQ ID NO 51
<211> LENGTH: 112
<212> TYPE: PRT
<213> ORGANISM: Artificial Sequence
<220> FEATURE:
<223> OTHER INFORMATION: modified antibody fragment

<400> SEQUENCE: 51

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 52
<211> LENGTH: 112
<212> TYPE: PRT
<213> ORGANISM: Artificial Sequence
<220> FEATURE:
```

<223> OTHER INFORMATION: modified antibody fragment

<400> SEQUENCE: 52

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 53
<211> LENGTH: 115
<212> TYPE: PRT
<213> ORGANISM: Artificial Sequence
<220> FEATURE:
<223> OTHER INFORMATION: modified antibody fragment

<400> SEQUENCE: 53

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Gly Leu Glu Trp Ile
        35                  40                  45

Gly Ala Ile Asp Pro Lys Thr Gly Asp Thr Ala Tyr Ser Gln Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 54
<211> LENGTH: 112
<212> TYPE: PRT
<213> ORGANISM: Artificial Sequence
<220> FEATURE:
<223> OTHER INFORMATION: modified antibody fragment

<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Arg Ala Ser Gly Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro

```
                    50                  55                  60
Asp Arg Phe Ser Gly Ser Gly Ser Gly Thr Asp Phe Thr Leu Thr Ile
 65                  70                  75                  80

Ser Ser Leu Gln Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
                100                 105                 110

<210> SEQ ID NO 55
<211> LENGTH: 448
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Ser
                 20                  25                  30

Trp Ile His Trp Val Arg Gln Ala Pro Gly Lys Gly Leu Glu Trp Val
             35                  40                  45

Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
```

-continued

```
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```